(12) United States Patent
Evans et al.

(10) Patent No.: US 9,788,882 B2
(45) Date of Patent: Oct. 17, 2017

(54) PLASMA BIPOLAR FORCEPS

(75) Inventors: Doug Evans, Austin, TX (US); Lloyd Gonzalez, Austin, TX (US); Nathan Wang, Austin, TX (US); Jean Woloszko, Austin, TX (US)

(73) Assignee: ArthroCare Corporation, Austin, TX (US)

( * ) Notice: Subject to any disclaimer, the term of this patent is extended or adjusted under 35 U.S.C. 154(b) by 935 days.

(21) Appl. No.: 13/608,387

(22) Filed: Sep. 10, 2012

(65) Prior Publication Data

US 2013/0066317 A1    Mar. 14, 2013

Related U.S. Application Data

(60) Provisional application No. 61/532,474, filed on Sep. 8, 2011.

(51) Int. Cl.
*A61B 18/18* (2006.01)
*A61B 18/04* (2006.01)
(Continued)

(52) U.S. Cl.
CPC ........ *A61B 18/042* (2013.01); *A61B 18/1442* (2013.01); *A61B 2018/0063* (2013.01);
(Continued)

(58) Field of Classification Search
CPC ....... A61B 17/28; A61B 17/285; A61B 17/29; A61B 17/295; A61B 17/32;
(Continued)

(56) References Cited

U.S. PATENT DOCUMENTS 2,050,904 A    8/1936    Talley ........................... 219/233
2,056,377 A    10/1939    Wappler ........................ 125/303
(Continued)

FOREIGN PATENT DOCUMENTS

CN    12222065    7/1999    ............. A61B 17/39
DE    3930451 A1    3/1991    ............. A61B 17/39
(Continued)

OTHER PUBLICATIONS

Barry et al., "The Effect of Radiofrequency-generated Thermal Energy on the Mechanical and Histologic Characteristics of the Arterial Wall in Vivo: Implications of Radiofrequency Angioplasty" *American Heart Journal* vol. 117, pp. 332-341, 1982.
(Continued)

*Primary Examiner* — Michael Carey
*Assistant Examiner* — Elizabeth K So
(74) *Attorney, Agent, or Firm* — David A. Warmbold

(57) ABSTRACT

An electrosurgical wand. At least some of the illustrative embodiments are electrosurgical wands configured as a surgical forceps including opposed legs that defines respective distal end portions, the legs of the forceps operable to be actuated between an open position and a closed position, an active and return electrode disposed on one of the respective distal end portions, a discharge aperture on one of the distal end portions coupled to a first fluid conduit, and an aspiration aperture through the return electrode on the other of the distal end portions fluidly coupled to a second fluid conduit. In embodiments, the position of the forceps' legs, and the electrical energy applied to the electrodes, is adjusted to provide dissection or coagulation to the tissue. A stop or latch on the forceps' legs may maintain the active and return electrode a fixed distance from one another.

19 Claims, 6 Drawing Sheets

(51) Int. Cl.
*A61B 18/14* (2006.01)
*A61B 18/00* (2006.01)
*A61B 18/16* (2006.01)

(52) U.S. Cl.
CPC .............. *A61B 2018/00577* (2013.01); *A61B 2018/00589* (2013.01); *A61B 2018/1472* (2013.01); *A61B 2018/162* (2013.01)

(58) Field of Classification Search
CPC ............ A61B 17/3201; A61B 17/3205; A61B 17/3209; A61B 18/00; A61B 18/04; A61B 18/12; A61B 18/14; A61B 18/16; A61B 18/18; A61B 2018/00577; A61B 2018/00583; A61B 2018/00589; A61B 2018/00595; A61B 2018/00601; A61B 2018/00607; A61B 2018/00613; A61B 2018/00625; A61B 2018/0063; A61B 2018/00636; A61B 2018/126; A61B 17/282; A61B 17/2926; A61B 17/2945; A61B 17/30; A61B 17/305; A61B 2018/146; A61B 2018/1462; A61B 2018/0225; A61B 18/085
USPC ..................................................... 606/51, 52
See application file for complete search history.

(56) References Cited

U.S. PATENT DOCUMENTS

| | | | |
|---|---|---|---|
| 3,633,425 A | 1/1972 | Sanford | 73/356 |
| 3,815,604 A | 6/1974 | O'Malley et al. | 128/305 |
| 3,828,780 A | 8/1974 | Morrison, Jr. et al. | 128/275 |
| 3,901,242 A | 8/1975 | Storz | 128/303 |
| 3,920,021 A | 11/1975 | Hiltebrandt | 128/303 |
| 3,939,839 A | 2/1976 | Curtiss | 128/303 |
| 3,970,088 A | 7/1976 | Morrison | 128/303 |
| 4,033,351 A | 7/1977 | Hetzel | 606/48 |
| 4,040,426 A | 8/1977 | Morrison, Jr. | 128/303 |
| 4,043,342 A | 8/1977 | Morrison, Jr. | 128/303 |
| 4,074,718 A | 2/1978 | Morrison, Jr. | 128/303 |
| 4,092,986 A | 6/1978 | Schneiderman | 128/303 |
| 4,116,198 A | 9/1978 | Roos | 128/303 |
| 4,181,131 A | 1/1980 | Ogiu | 128/303 |
| 4,184,492 A | 1/1980 | Meinke et al. | 128/303 |
| 4,202,337 A | 5/1980 | Hren et al. | 128/303 |
| 4,228,800 A | 10/1980 | Degler, Jr. et al. | 128/303 |
| 4,232,676 A | 11/1980 | Herczog | 128/303 |
| 4,248,231 A | 2/1981 | Herczog et al. | 128/303 |
| 4,301,802 A | 11/1981 | Poler | 606/48 |
| 4,326,529 A | 4/1982 | Doss et al. | 128/303 |
| 4,381,007 A | 4/1983 | Doss | 128/303 |
| 4,474,179 A | 10/1984 | Koch | 606/40 |
| 4,476,862 A | 10/1984 | Pao | 128/303 |
| 4,532,924 A | 8/1985 | Auth et al. | 128/303 |
| 4,548,207 A | 10/1985 | Reimels | 128/303 |
| 4,567,890 A | 2/1986 | Ohta et al. | 128/303 |
| 4,582,057 A | 4/1986 | Auth et al. | 606/31 |
| 4,590,934 A | 5/1986 | Malis et al. | 128/303 |
| 4,593,691 A | 6/1986 | Lindstrom et al. | 128/303 |
| 4,658,817 A | 4/1987 | Hardy | 606/14 |
| 4,660,571 A | 4/1987 | Hess et al. | 128/784 |
| 4,674,499 A | 6/1987 | Pao | 128/303 |
| 4,682,596 A | 7/1987 | Bales et al. | 128/303 |
| 4,706,667 A | 11/1987 | Roos | 128/303 |
| 4,709,698 A | 12/1987 | Johnston et al. | 606/41 |
| 4,727,874 A | 3/1988 | Bowers et al. | 128/303 |
| 4,765,331 A | 8/1988 | Petruzzi et al. | 128/303 |
| 4,785,823 A | 11/1988 | Eggers et al. | 128/692 |
| 4,805,616 A | 2/1989 | Pao | 128/303 |
| 4,823,791 A | 4/1989 | D'Amelio et al. | 123/303 |
| 4,832,048 A | 5/1989 | Cohen | 128/786 |
| 4,860,752 A | 8/1989 | Turner | 607/102 |
| 4,907,589 A | 3/1990 | Cosman | 606/34 |
| 4,920,978 A | 5/1990 | Colvin | 128/784 |
| 4,931,047 A | 6/1990 | Broadwin et al. | 604/22 |
| 4,936,281 A | 6/1990 | Stasz | 128/660 |
| 4,936,301 A | 6/1990 | Rexroth et al. | 606/45 |
| 4,943,290 A | 7/1990 | Rexroth et al. | 606/45 |
| 4,966,597 A | 10/1990 | Cosman | 606/50 |
| 4,967,765 A | 11/1990 | Turner et al. | 128/785 |
| 4,976,711 A | 12/1990 | Parins et al. | 606/48 |
| 4,979,948 A | 12/1990 | Geddes et al. | 606/33 |
| 4,998,933 A | 3/1991 | Eggers et al. | 606/41 |
| 5,007,908 A | 4/1991 | Rydell | 606/47 |
| 5,009,656 A | 4/1991 | Reimels | 606/48 |
| 5,035,696 A | 7/1991 | Rydell | 606/47 |
| 5,047,026 A | 9/1991 | Rydell | 606/48 |
| 5,047,027 A | 9/1991 | Rydell | 606/48 |
| 5,057,105 A | 10/1991 | Malone et al. | 606/28 |
| 5,057,106 A | 10/1991 | Kasevich et al. | 606/33 |
| 5,078,716 A | 1/1992 | Doll | 606/47 |
| 5,078,717 A | 1/1992 | Parins et al. | 606/48 |
| 5,080,660 A | 1/1992 | Buelna | 606/45 |
| 5,083,565 A | 1/1992 | Parins | 600/374 |
| 5,084,044 A | 1/1992 | Quint | 606/27 |
| 5,085,659 A | 2/1992 | Rydell | 606/47 |
| 5,088,997 A | 2/1992 | Delahuerga et al. | 606/42 |
| 5,098,431 A | 3/1992 | Rydell | 606/48 |
| 5,099,840 A | 3/1992 | Goble | 128/422 |
| 5,102,410 A | 4/1992 | Dressel | 606/15 |
| 5,108,391 A | 4/1992 | Flachenecker et al. | 606/38 |
| RE33,925 E | 5/1992 | Bales et al. | 606/48 |
| 5,112,330 A | 5/1992 | Nishigaki et al. | 606/46 |
| 5,122,138 A | 6/1992 | Manwaring | 606/46 |
| 5,125,928 A | 6/1992 | Parins et al. | 606/48 |
| 5,156,151 A | 10/1992 | Imran | 600/375 |
| 5,167,659 A | 12/1992 | Ohtomo et al. | 606/40 |
| 5,167,660 A | 12/1992 | Altendorf | 606/40 |
| 5,171,311 A | 12/1992 | Rydell et al. | 606/48 |
| 5,178,620 A | 1/1993 | Eggers et al. | 606/41 |
| 5,190,517 A | 3/1993 | Zieve et al. | 604/22 |
| 5,192,280 A | 3/1993 | Parins | 606/48 |
| 5,195,959 A | 3/1993 | Smith | 604/34 |
| 5,195,968 A | 3/1993 | Lundquist et al. | 604/95.04 |
| 5,196,007 A | 3/1993 | Ellman | 606/32 |
| 5,197,466 A | 3/1993 | Marchosky et al. | 128/399 |
| 5,197,963 A | 3/1993 | Parins | 606/46 |
| 5,207,675 A | 5/1993 | Canady | 606/40 |
| 5,217,457 A | 6/1993 | Delahuerga et al. | 606/42 |
| 5,217,459 A | 6/1993 | Kamerling | 606/48 |
| 5,249,585 A | 10/1993 | Turner et al. | 607/99 |
| 5,261,410 A | 11/1993 | Alfano et al. | 600/475 |
| 5,267,994 A | 12/1993 | Gentelia et al. | 606/15 |
| 5,267,997 A | 12/1993 | Farin et al. | 606/38 |
| 5,273,524 A | 12/1993 | Fox et al. | 604/21 |
| 5,277,201 A | 1/1994 | Stern | 607/98 |
| 5,281,216 A | 1/1994 | Klicek | 606/42 |
| 5,281,218 A | 1/1994 | Imran | 606/41 |
| 5,290,282 A | 3/1994 | Casscells | 606/29 |
| 5,300,069 A | 4/1994 | Hunsberger et al. | 606/37 |
| 5,306,238 A | 4/1994 | Fleenor | 606/42 |
| 5,312,400 A | 5/1994 | Bales et al. | 606/41 |
| 5,314,406 A | 5/1994 | Arias et al. | 604/21 |
| 5,324,254 A | 6/1994 | Phillips | 604/21 |
| 5,330,470 A | 7/1994 | Hagen | 606/42 |
| 5,334,140 A | 8/1994 | Phillips | 604/35 |
| 5,334,183 A | 8/1994 | Wuchinich | 606/46 |
| 5,334,193 A | 8/1994 | Nardella | 606/41 |
| 5,336,220 A | 8/1994 | Ryan et al. | 604/22 |
| 5,336,443 A | 8/1994 | Odashima | 252/511 |
| 5,342,357 A | 8/1994 | Nardella | 606/40 |
| 5,363,861 A | 11/1994 | Edwards et al. | 600/585 |
| 5,366,443 A | 11/1994 | Eggers et al. | 604/114 |
| 5,370,675 A | 12/1994 | Edwards et al. | 607/101 |
| 5,374,261 A | 12/1994 | Yoon | 604/385.01 |
| 5,375,588 A | 12/1994 | Yoon | 128/4 |
| 5,380,277 A | 1/1995 | Phillips | 604/33 |
| 5,380,316 A | 1/1995 | Aita | 606/7 |
| 5,383,876 A | 1/1995 | Nardella | 606/49 |
| 5,383,917 A | 1/1995 | Desai et al. | 607/702 |
| 5,389,096 A | 2/1995 | Aita | 606/15 |
| 5,395,312 A | 3/1995 | Desai | 604/22 |

(56) References Cited

U.S. PATENT DOCUMENTS

| | | | |
|---|---|---|---|
| 5,395,363 A | 3/1995 | Billings et al. | 606/41 |
| 5,395,368 A | 3/1995 | Ellman et al. | 606/45 |
| 5,400,267 A | 3/1995 | Denen et al. | 702/59 |
| 5,401,272 A | 3/1995 | Perkins | 606/15 |
| 5,403,311 A | 4/1995 | Abele et al. | 606/49 |
| 5,417,687 A | 5/1995 | Nardella et al. | 606/32 |
| 5,419,767 A | 5/1995 | Eggers et al. | 604/114 |
| 5,423,810 A | 6/1995 | Goble et al. | 606/40 |
| 5,423,811 A | 6/1995 | Imran et al. | 606/41 |
| 5,423,812 A | 6/1995 | Ellman et al. | 606/45 |
| 5,423,882 A | 6/1995 | Jackman et al. | 607/122 |
| 5,436,566 A | 7/1995 | Thompson et al. | 324/713 |
| 5,437,662 A | 8/1995 | Nardella | 606/40 |
| 5,438,302 A | 8/1995 | Goble | 331/167 |
| 5,441,499 A | 8/1995 | Fritzsch | 606/45 |
| 5,451,224 A | 9/1995 | Goble et al. | 606/48 |
| 5,454,809 A | 10/1995 | Janssen | 606/41 |
| 5,456,662 A | 10/1995 | Edwards et al. | 604/22 |
| 5,458,596 A | 10/1995 | Lax et al. | 606/31 |
| 5,487,757 A | 1/1996 | Truckai et al. | 604/264 |
| 5,490,850 A | 2/1996 | Ellman et al. | 606/45 |
| 5,496,312 A | 3/1996 | Klicek | 606/34 |
| 5,496,314 A | 3/1996 | Eggers | 606/41 |
| 5,496,317 A | 3/1996 | Goble et al. | 606/48 |
| 5,505,728 A | 4/1996 | Ellman et al. | 606/39 |
| 5,505,730 A | 4/1996 | Edwards | 606/41 |
| 5,514,130 A | 5/1996 | Baker | 606/41 |
| 5,554,152 A | 9/1996 | Aita | 606/7 |
| 5,556,397 A | 9/1996 | Long et al. | 606/48 |
| 5,562,503 A | 10/1996 | Ellman et al. | 439/638 |
| 5,562,703 A | 10/1996 | Desai | 606/210 |
| 5,569,242 A | 10/1996 | Lax et al. | 606/42 |
| 5,571,100 A | 11/1996 | Goble et al. | 606/41 |
| 5,571,101 A | 11/1996 | Ellman et al. | 606/45 |
| 5,584,872 A | 12/1996 | LaFontaine et al. | 607/117 |
| 5,609,151 A | 3/1997 | Mulier et al. | 128/642 |
| 5,624,439 A | 4/1997 | Edwards et al. | 606/45 |
| 5,630,812 A | 5/1997 | Ellman et al. | 606/41 |
| 5,633,578 A | 5/1997 | Eggers et al. | 323/301 |
| 5,647,869 A | 7/1997 | Goble et al. | 606/37 |
| 5,658,278 A | 8/1997 | Imran et al. | 606/41 |
| 5,662,680 A | 9/1997 | Desai | 606/210 |
| 5,674,191 A | 10/1997 | Edwards et al. | 604/22 |
| 5,676,693 A | 10/1997 | LaFontaine et al. | 607/116 |
| 5,681,282 A | 10/1997 | Eggers et al. | 604/114 |
| 5,683,366 A | 11/1997 | Eggers et al. | 604/114 |
| 5,683,386 A | 11/1997 | Ellman et al. | 606/41 |
| 5,683,387 A | 11/1997 | Garito et al. | 606/45 |
| 5,688,267 A | 11/1997 | Panescu et al. | 606/41 |
| 5,695,495 A | 12/1997 | Ellman et al. | 606/41 |
| 5,697,281 A | 12/1997 | Eggers et al. | 604/114 |
| 5,697,536 A | 12/1997 | Eggers et al. | 604/114 |
| 5,697,882 A | 12/1997 | Eggers et al. | 604/114 |
| 5,697,909 A | 12/1997 | Eggers et al. | 604/114 |
| 5,700,262 A | 12/1997 | Acosta et al. | 606/48 |
| 5,707,349 A | 1/1998 | Edwards | 604/22 |
| 5,718,702 A | 2/1998 | Edwards | 606/41 |
| 5,725,524 A | 3/1998 | Mulier et al. | 606/41 |
| 5,728,094 A | 3/1998 | Edwards | 606/41 |
| 5,733,282 A | 3/1998 | Ellman et al. | 606/45 |
| 5,738,114 A | 4/1998 | Edwards | 128/898 |
| 5,743,870 A | 4/1998 | Edwards | 604/22 |
| 5,746,224 A | 5/1998 | Edwards | 128/898 |
| 5,749,869 A | 5/1998 | Lindenmeier et al. | 606/34 |
| 5,766,153 A | 6/1998 | Eggers et al. | 604/114 |
| 5,775,338 A | 7/1998 | Hastings | 128/898 |
| 5,776,128 A | 7/1998 | Eggers | 606/48 |
| 5,782,828 A | 7/1998 | Chen et al. | 606/42 |
| 5,800,379 A | 9/1998 | Edwards | 604/22 |
| 5,800,429 A | 9/1998 | Edwards | 606/41 |
| 5,807,395 A | 9/1998 | Mulier et al. | 606/41 |
| 5,810,764 A | 9/1998 | Eggers et al. | 604/23 |
| 5,810,809 A | 9/1998 | Rydell | 606/49 |
| 5,817,049 A | 10/1998 | Edwards | 604/22 |
| 5,820,580 A | 10/1998 | Edwards et al. | 604/22 |
| 5,823,197 A | 10/1998 | Edwards | 128/898 |
| 5,827,277 A | 10/1998 | Edwards | 606/41 |
| 5,836,875 A | 11/1998 | Webster, Jr. | 600/374 |
| 5,843,019 A | 12/1998 | Eggers et al. | 604/22 |
| 5,843,021 A | 12/1998 | Edwards et al. | 604/22 |
| 5,843,077 A | 12/1998 | Edwards | 606/41 |
| 5,860,951 A | 1/1999 | Eggers | 604/510 |
| 5,860,974 A | 1/1999 | Abele | 606/41 |
| 5,860,975 A | 1/1999 | Goble et al. | 606/45 |
| 5,871,469 A | 2/1999 | Eggers et al. | 604/114 |
| 5,873,855 A | 2/1999 | Eggers et al. | 604/114 |
| 5,879,349 A | 3/1999 | Edwards | 606/45 |
| 5,885,277 A | 3/1999 | Korth | 606/35 |
| 5,888,198 A | 3/1999 | Eggers et al. | 604/114 |
| 5,891,095 A | 4/1999 | Eggers et al. | 604/114 |
| 5,891,134 A | 4/1999 | Goble et al. | 606/27 |
| 5,897,553 A | 4/1999 | Mulier | 606/41 |
| 5,902,272 A | 5/1999 | Eggers et al. | 604/114 |
| 5,916,214 A | 6/1999 | Cosio et al. | 606/41 |
| 5,919,190 A | 7/1999 | Vandusseldorp | 606/46 |
| 5,921,983 A | 7/1999 | Shannon, Jr. | 606/45 |
| 5,944,715 A | 8/1999 | Goble et al. | 606/41 |
| 5,954,716 A | 9/1999 | Sharkey et al. | 606/32 |
| 5,988,171 A | 11/1999 | Sohn et al. | 128/848 |
| 6,004,319 A | 12/1999 | Goble et al. | 606/48 |
| 6,006,755 A | 12/1999 | Edwards | 128/898 |
| 6,009,877 A | 1/2000 | Edwards | 128/898 |
| 6,013,076 A | 1/2000 | Goble et al. | 606/41 |
| 6,015,406 A | 1/2000 | Goble et al. | 606/41 |
| 6,024,733 A | 2/2000 | Eggers et al. | 604/500 |
| 6,026,816 A | 2/2000 | McMillan et al. | 128/898 |
| 6,027,501 A | 2/2000 | Goble et al. | 606/41 |
| 6,032,674 A | 3/2000 | Eggers et al. | 128/898 |
| 6,039,734 A | 3/2000 | Goble et al. | 606/41 |
| 6,044,846 A | 4/2000 | Edwards | 128/898 |
| 6,047,700 A | 4/2000 | Eggers et al. | 128/898 |
| 6,053,172 A | 4/2000 | Hovda et al. | 128/898 |
| 6,056,746 A | 5/2000 | Goble et al. | 606/48 |
| 6,063,079 A | 5/2000 | Hovda et al. | 606/41 |
| 6,066,134 A | 5/2000 | Eggers et al. | 606/32 |
| 6,066,139 A | 5/2000 | Ryan et al. | 606/50 |
| 6,068,628 A | 5/2000 | Fanton et al. | 606/41 |
| 6,071,281 A | 6/2000 | Burnside et al. | 606/41 |
| 6,073,052 A | 6/2000 | Zelickson et al. | 607/100 |
| 6,074,386 A | 6/2000 | Goble et al. | 606/34 |
| 6,086,585 A | 7/2000 | Hovda et al. | 606/45 |
| 6,090,106 A | 7/2000 | Goble et al. | 606/41 |
| 6,093,186 A | 7/2000 | Goble et al. | 606/34 |
| 6,102,046 A | 8/2000 | Weinstein et al. | 128/898 |
| 6,105,581 A | 8/2000 | Eggers et al. | 128/898 |
| 6,109,268 A | 8/2000 | Thapliyal et al. | 128/898 |
| 6,117,109 A | 9/2000 | Eggers et al. | 604/114 |
| 6,126,682 A | 10/2000 | Sharkey et al. | 607/96 |
| 6,142,992 A | 11/2000 | Cheng et al. | 606/34 |
| 6,149,620 A | 11/2000 | Baker et al. | 604/22 |
| 6,159,194 A | 12/2000 | Eggers et al. | 604/500 |
| 6,159,208 A | 12/2000 | Hovda et al. | 606/41 |
| 6,168,593 B1 | 1/2001 | Sharkey et al. | 606/34 |
| 6,174,309 B1 | 1/2001 | Wrublewski et al. | 606/45 |
| 6,179,824 B1 | 1/2001 | Eggers et al. | 604/500 |
| 6,179,836 B1 | 1/2001 | Eggers et al. | 606/45 |
| 6,183,469 B1 | 2/2001 | Thapliyal et al. | 606/41 |
| 6,190,381 B1 | 2/2001 | Olsen et al. | 606/32 |
| 6,203,542 B1 | 3/2001 | Ellsberry et al. | 606/41 |
| 6,210,402 B1 | 4/2001 | Olsen et al. | 606/32 |
| 6,210,405 B1 | 4/2001 | Goble et al. | 606/41 |
| 6,224,592 B1 | 5/2001 | Eggers et al. | 606/32 |
| 6,228,078 B1 | 5/2001 | Eggers | 606/32 |
| 6,228,081 B1 | 5/2001 | Goble | 606/34 |
| 6,234,178 B1 | 5/2001 | Goble et al. | 128/898 |
| 6,235,020 B1 | 5/2001 | Cheng et al. | 606/34 |
| 6,237,604 B1 | 5/2001 | Burnside et al. | 128/897 |
| 6,238,391 B1 | 5/2001 | Olsen et al. | 606/41 |
| 6,254,600 B1 | 7/2001 | Willink et al. | 606/41 |
| 6,258,086 B1 | 7/2001 | Ashley et al. | 606/41 |
| 6,261,286 B1 | 7/2001 | Goble et al. | 606/34 |
| 6,261,311 B1 | 7/2001 | Sharkey et al. | 607/96 |
| 6,264,652 B1 | 7/2001 | Eggers et al. | 606/41 |
| 6,270,460 B1 | 8/2001 | McCartan et al. | 600/459 |

(56) References Cited

U.S. PATENT DOCUMENTS

| | | | |
|---|---|---|---|
| 6,270,476 B1 | 8/2001 | Santoianni et al. | 604/95.04 |
| 6,277,112 B1 | 8/2001 | Underwood et al. | 606/32 |
| 6,280,441 B1 | 8/2001 | Ryan | 606/45 |
| 6,283,961 B1 | 9/2001 | Underwood et al. | 606/41 |
| 6,293,942 B1 | 9/2001 | Goble et al. | 606/38 |
| 6,296,636 B1 | 10/2001 | Cheng et al. | 606/32 |
| 6,296,638 B1 | 10/2001 | Davison et al. | 606/41 |
| 6,306,134 B1 | 10/2001 | Goble et al. | 606/42 |
| 6,308,089 B1 | 10/2001 | von der Rur et al. | 600/338 |
| 6,309,387 B1 | 10/2001 | Eggers et al. | 606/41 |
| 6,312,408 B1 | 11/2001 | Eggers et al. | 604/114 |
| 6,322,549 B1 | 11/2001 | Eggers et al. | 604/500 |
| 6,355,032 B1 | 3/2002 | Hovda et al. | 606/32 |
| 6,363,937 B1 | 4/2002 | Hovda et al. | 128/898 |
| 6,364,877 B1 | 4/2002 | Goble et al. | 606/34 |
| 6,379,350 B1 | 4/2002 | Sharkey et al. | 606/41 |
| 6,379,351 B1 | 4/2002 | Thapliyal et al. | 606/41 |
| 6,387,093 B1 | 5/2002 | Ellman et al. | 606/39 |
| 6,391,025 B1 | 5/2002 | Weinstein et al. | 606/41 |
| 6,411,852 B1 | 6/2002 | Danek et al. | 607/42 |
| 6,413,254 B1 | 7/2002 | Hissong et al. | 606/27 |
| 6,416,491 B1 | 7/2002 | Edwards et al. | 606/41 |
| 6,416,507 B1 | 7/2002 | Eggers et al. | 606/32 |
| 6,416,508 B1 | 7/2002 | Eggers et al. | 606/32 |
| 6,416,509 B1 | 7/2002 | Goble et al. | 606/37 |
| 6,427,089 B1 | 7/2002 | Knowlton | 607/101 |
| 6,432,103 B1 | 8/2002 | Ellsberry et al. | 606/41 |
| 6,464,699 B1 | 10/2002 | Swanson | 606/41 |
| 6,468,274 B1 | 10/2002 | Alleyne et al. | 606/32 |
| 6,468,275 B1 | 10/2002 | Wampler et al. | 606/48 |
| 6,482,201 B1 | 11/2002 | Olsen et al. | 606/41 |
| 6,491,690 B1 | 12/2002 | Goble et al. | 606/41 |
| 6,517,498 B1 | 2/2003 | Burbank et al. | 600/564 |
| 6,530,922 B2 | 3/2003 | Cosman | 606/34 |
| 6,530,924 B1 | 3/2003 | Ellman et al. | 606/45 |
| 6,551,032 B1 | 4/2003 | Nolan et al. | 407/13 |
| 6,572,613 B1 | 6/2003 | Ellman et al. | 606/45 |
| 6,578,579 B2 | 6/2003 | Burnside | 128/897 |
| 6,589,235 B2 | 7/2003 | Wong et al. | 606/32 |
| 6,589,237 B2 | 7/2003 | Woloszko et al. | 606/41 |
| 6,602,248 B1 | 8/2003 | Sharps et al. | 606/32 |
| 6,620,156 B1 | 9/2003 | Garito et al. | 606/50 |
| 6,632,193 B1 | 10/2003 | Davison et al. | 604/22 |
| 6,632,220 B1 | 10/2003 | Eggers et al. | 606/41 |
| 6,702,810 B2 | 3/2004 | McClurken et al. | 606/34 |
| 6,736,810 B2 | 5/2004 | Hoey et al. | 606/34 |
| 6,746,447 B2 | 6/2004 | Davison et al. | 606/41 |
| 6,749,604 B1 | 6/2004 | Eggers et al. | 606/41 |
| 6,749,608 B2 | 6/2004 | Garito et al. | 606/45 |
| 6,770,071 B2 | 8/2004 | Woloszko et al. | 606/41 |
| 6,780,178 B2 | 8/2004 | Palanker et al. | 600/41 |
| 6,780,180 B1 | 8/2004 | Goble et al. | 606/41 |
| 6,802,842 B2 | 10/2004 | Ellman et al. | 606/45 |
| 6,837,887 B2 | 1/2005 | Woloszko et al. | 606/41 |
| 6,837,888 B2 | 1/2005 | Ciarrocca et al. | 606/41 |
| 6,896,674 B1 | 5/2005 | Woloszko et al. | 606/41 |
| 6,920,883 B2 | 7/2005 | Bessette et al. | 128/898 |
| 6,929,640 B1 | 8/2005 | Underwood et al. | 606/32 |
| 6,942,662 B2 | 9/2005 | Goble et al. | 606/48 |
| 6,949,096 B2 | 9/2005 | Davison et al. | 606/41 |
| 6,955,172 B2 | 10/2005 | Nelson et al. | 128/848 |
| 6,960,204 B2 | 11/2005 | Eggers et al. | 606/32 |
| 6,974,453 B2 | 12/2005 | Woloszko et al. | 606/41 |
| 6,984,231 B2 | 1/2006 | Goble et al. | 606/37 |
| 6,991,631 B2 | 1/2006 | Woloszko et al. | 606/41 |
| 7,004,941 B2 | 2/2006 | Tvinnereim et al. | 606/41 |
| 7,041,102 B2 | 5/2006 | Truckai et al. | 606/51 |
| 7,066,936 B2 | 6/2006 | Ryan | 606/32 |
| 7,070,596 B1 | 7/2006 | Woloszko et al. | 606/41 |
| 7,090,672 B2 | 8/2006 | Underwood et al. | 606/41 |
| 7,094,215 B2 | 8/2006 | Davison et al. | 604/22 |
| 7,104,986 B2 | 9/2006 | Hovda et al. | 606/32 |
| 7,131,969 B1 | 11/2006 | Hovda et al. | 606/45 |
| 7,160,296 B2 | 1/2007 | Pearson et al. | 606/42 |
| 7,169,143 B2 | 1/2007 | Eggers et al. | 606/32 |
| 7,179,255 B2 | 2/2007 | Lettice et al. | 606/32 |
| 7,186,234 B2 | 3/2007 | Dahla et al. | 604/22 |
| 7,192,428 B2 | 3/2007 | Eggers et al. | 606/41 |
| 7,195,630 B2 | 3/2007 | Ciarrocca | 606/48 |
| 7,201,750 B1 | 4/2007 | Eggers et al. | 606/41 |
| 7,217,268 B2 | 5/2007 | Eggers et al. | 606/32 |
| 7,235,073 B2 * | 6/2007 | Levine | A61B 18/1442 606/25 |
| 7,241,293 B2 | 7/2007 | Davison | 600/410 |
| 7,270,658 B2 | 9/2007 | Woloszko et al. | 606/32 |
| 7,270,659 B2 | 9/2007 | Ricart et al. | 606/32 |
| 7,270,661 B2 | 9/2007 | Dahla et al. | 606/41 |
| 7,276,063 B2 | 10/2007 | Davison et al. | 606/45 |
| 7,297,143 B2 | 11/2007 | Woloszko et al. | 606/41 |
| 7,297,145 B2 | 11/2007 | Woloszko et al. | 606/41 |
| 7,318,823 B2 | 1/2008 | Sharps et al. | 606/32 |
| 7,331,956 B2 | 2/2008 | Hovda et al. | 606/32 |
| RE40,156 E | 3/2008 | Sharps et al. | 606/32 |
| 7,357,798 B2 | 4/2008 | Sharps et al. | 606/32 |
| 7,387,625 B2 | 6/2008 | Hovda et al. | 606/32 |
| 7,419,488 B2 | 9/2008 | Ciarrocca et al. | 606/41 |
| 7,429,260 B2 | 9/2008 | Underwood et al. | 606/32 |
| 7,429,262 B2 | 9/2008 | Woloszko et al. | 606/46 |
| 7,435,247 B2 | 10/2008 | Woloszko et al. | 604/45 |
| 7,442,191 B2 | 10/2008 | Hovda et al. | 606/41 |
| 7,445,618 B2 | 11/2008 | Eggers et al. | 604/48 |
| 7,449,021 B2 | 11/2008 | Underwood et al. | 606/32 |
| 7,462,178 B2 | 12/2008 | Woloszko et al. | 607/105 |
| 7,468,059 B2 | 12/2008 | Eggers et al. | 606/32 |
| 7,491,200 B2 | 2/2009 | Underwood et al. | 606/32 |
| 7,507,236 B2 | 3/2009 | Eggers et al. | 606/41 |
| 7,572,251 B1 | 8/2009 | Davison et al. | 604/500 |
| 7,632,267 B2 | 12/2009 | Dahla | 606/41 |
| 7,691,101 B2 | 4/2010 | Davison et al. | 606/41 |
| 7,704,249 B2 | 4/2010 | Woloszko et al. | 606/48 |
| 7,708,733 B2 | 5/2010 | Sanders et al. | 606/41 |
| 7,824,398 B2 | 11/2010 | Woloszko et al. | 606/45 |
| 7,879,034 B2 | 2/2011 | Woloszko et al. | 606/48 |
| 7,892,230 B2 | 2/2011 | Woloszko et al. | 606/41 |
| 7,901,403 B2 | 3/2011 | Woloszko et al. | 606/48 |
| 8,012,153 B2 | 9/2011 | Woloszko et al. | 606/48 |
| 8,114,071 B2 | 2/2012 | Woloszko et al. | 606/32 |
| 8,469,991 B2 * | 6/2013 | Kerr | 606/205 |
| 8,568,405 B2 | 10/2013 | Cox et al. | 606/41 |
| 8,747,401 B2 | 6/2014 | Gonzalez et al. | 606/41 |
| 9,011,428 B2 | 4/2015 | Nguyen et al. | 606/41 |
| 2002/0026186 A1 | 2/2002 | Woloszko et al. | 606/41 |
| 2002/0029036 A1 | 3/2002 | Goble et al. | 606/38 |
| 2002/0049438 A1 | 4/2002 | Sharkey et al. | 606/41 |
| 2002/0111608 A1 * | 8/2002 | Baerveldt | A61F 9/00781 606/41 |
| 2002/0120259 A1 | 8/2002 | Lettice et al. | 606/32 |
| 2003/0013986 A1 | 1/2003 | Saadat | 600/549 |
| 2003/0014050 A1 | 1/2003 | Sharkey et al. | 606/45 |
| 2003/0088245 A1 | 5/2003 | Woloszko et al. | 606/32 |
| 2003/0097129 A1 | 5/2003 | Davison et al. | 606/41 |
| 2003/0158545 A1 | 8/2003 | Hovda et al. | 606/32 |
| 2003/0171743 A1 | 9/2003 | Tasto et al. | 606/32 |
| 2003/0208196 A1 | 11/2003 | Stone | 606/41 |
| 2003/0212396 A1 | 11/2003 | Eggers et al. | 606/41 |
| 2004/0054366 A1 | 3/2004 | Davison et al. | 606/39 |
| 2004/0116922 A1 | 6/2004 | Hovda et al. | 606/41 |
| 2004/0127893 A1 | 7/2004 | Hovda | 606/41 |
| 2004/0230190 A1 | 11/2004 | Dahla et al. | 604/41 |
| 2005/0004634 A1 | 1/2005 | Ricart et al. | 606/41 |
| 2005/0043728 A1 | 2/2005 | Ciarrocca | 606/48 |
| 2005/0119650 A1 | 6/2005 | Sanders et al. | 606/41 |
| 2005/0261754 A1 | 11/2005 | Woloszko et al. | 606/32 |
| 2005/0283149 A1 | 12/2005 | Thorne et al. | 606/48 |
| 2005/0288665 A1 | 12/2005 | Woloszko et al. | 606/41 |
| 2006/0036237 A1 | 2/2006 | Davison et al. | 606/41 |
| 2006/0095031 A1 | 5/2006 | Ormsby | 606/34 |
| 2006/0129145 A1 | 6/2006 | Woloszko et al. | 606/41 |
| 2006/0189971 A1 | 8/2006 | Tasto et al. | 606/32 |
| 2006/0253117 A1 | 11/2006 | Hovda et al. | 128/898 |
| 2006/0259025 A1 | 11/2006 | Dahla | 607/108 |
| 2006/0259031 A1 | 11/2006 | Carmel et al. | 606/41 |
| 2007/0010808 A1 | 1/2007 | Dahla | 606/41 |
| 2007/0106288 A1 | 5/2007 | Woloszko et al. | 606/41 |

(56) References Cited

U.S. PATENT DOCUMENTS

| | | | |
|---|---|---|---|
| 2007/0149966 A1 | 6/2007 | Dahla et al. | 606/41 |
| 2007/0161981 A1 | 7/2007 | Sanders et al. | 606/41 |
| 2007/0208335 A1 | 9/2007 | Woloszko et al. | 606/41 |
| 2007/0282323 A1 | 12/2007 | Woloszko et al. | 606/41 |
| 2008/0200972 A1 | 8/2008 | Rittman et al. | 607/117 |
| 2009/0030414 A1* | 1/2009 | Bayat | A61B 18/1442 606/51 |
| 2010/0204690 A1 | 8/2010 | Bigley et al. | 606/41 |
| 2012/0101494 A1 | 4/2012 | Cadouri et al. | 606/41 |
| 2012/0191089 A1 | 7/2012 | Gonzalez et al. | 606/45 |
| 2012/0203219 A1 | 8/2012 | Evans et al. | 606/33 |
| 2012/0226273 A1 | 9/2012 | Nguyen et al. | 606/41 |
| 2013/0197506 A1 | 8/2013 | Evans et al. | 606/48 |
| 2014/0200581 A1 | 7/2014 | Aluru et al. | 606/48 |
| 2015/0196346 A1 | 7/2015 | Nguyen et al. | A61B 18/042 |

FOREIGN PATENT DOCUMENTS

| | | | |
|---|---|---|---|
| DE | 202014002299.20 | 7/2014 | A61B 18/12 |
| DE | 102014003645.00 | 9/2014 | A61B 18/12 |
| EP | 0509670 | 10/1992 | A61B 17/39 |
| EP | 0703461 A2 | 3/1996 | G01B 27/02 |
| EP | 0740926 A2 | 11/1996 | A61B 17/39 |
| EP | 0754437 A2 | 1/1997 | A61B 17/39 |
| EP | 0694290 B1 | 11/2000 | A61B 18/04 |
| EP | 0959787 | 10/2007 | A61B 18/00 |
| EP | 2198799 | 6/2010 | A61B 18/14 |
| FR | 2313949 | 1/1977 | A61N 3/02 |
| GB | 2 308 979 | 7/1997 | A61B 17/36 |
| GB | 2 308 980 | 7/1997 | A61B 17/36 |
| GB | 2 308 981 | 7/1997 | A61B 17/36 |
| GB | 2 327 350 | 1/1999 | A61B 17/39 |
| GB | 2 327 351 | 1/1999 | A61B 17/39 |
| GB | 2 327 352 | 1/1999 | A61B 17/39 |
| GB | 2477353 | 8/2011 | A61B 18/14 |
| GB | 2479582 | 10/2011 | A61B 18/14 |
| GB | 2488039 | 8/2012 | A61B 18/14 |
| GB | 2522352 | 2/2015 | A61B 18/14 |
| JP | 57-57802 | 4/1982 | A61B 1/00 |
| JP | 57-117843 | 7/1982 | A61B 17/39 |
| JP | 58-13213 | 1/1983 | A61B 18/12 |
| JP | 10-43198 | 2/1998 | A61B 17/42 |
| WO | 90/03152 | 4/1990 | A61B 17/39 |
| WO | 90/07303 | 7/1990 | A61B 17/39 |
| WO | 92/21278 | 12/1992 | A61B 5/04 |
| WO | 93/13816 | 7/1993 | A61B 17/36 |
| WO | 93/20747 | 10/1993 | A61B 5/00 |
| WO | 94/04220 | 3/1994 | A61N 1/06 |
| WO | 94/08654 | 4/1994 | A61M 37/00 |
| WO | 94/10924 | 5/1994 | A61B 17/39 |
| WO | 94/26228 | 11/1994 | A61G 17/36 |
| WO | 95/34259 | 12/1995 | A61F 5/48 |
| WO | 96/00042 | 1/1996 | A61B 17/39 |
| WO | 96/23449 | 8/1996 | A61B 17/39 |
| WO | 96/37156 | 11/1996 | A61B 17/00 |
| WO | 96/39914 | 12/1996 | A61B 1/00 |
| WO | 97/00646 | 1/1997 | A61B 17/39 |
| WO | 97/00647 | 1/1997 | A61B 17/39 |
| WO | 97/15237 | 5/1997 | A61B 18/12 |
| WO | 97/18765 | 5/1997 | A61B 17/36 |
| WO | 97/24073 | 7/1997 | A61B 17/39 |
| WO | 97/24074 | 7/1997 | A61B 17/39 |
| WO | 97/24993 | 7/1997 | A61B 17/39 |
| WO | 97/24994 | 7/1997 | A61B 17/39 |
| WO | 97/30644 | 8/1997 | A61B 17/39 |
| WO | 97/30645 | 8/1997 | A61B 17/39 |
| WO | 97/30646 | 8/1997 | A61B 17/39 |
| WO | 97/30647 | 8/1997 | A61B 17/39 |
| WO | 97/41785 | 11/1997 | A61B 17/39 |
| WO | 97/41786 | 11/1997 | A61B 17/39 |
| WO | 97/41787 | 11/1997 | A61B 17/39 |
| WO | 97/41788 | 11/1997 | A61B 17/39 |
| WO | 97/43969 | 11/1997 | A61B 17/39 |
| WO | 97/43970 | 11/1997 | A61B 17/39 |
| WO | 97/43972 | 11/1997 | A61B 17/39 |
| WO | 97/43973 | 11/1997 | A61B 17/39 |
| WO | 97/44092 | 11/1997 | A61B 17/39 |
| WO | 97/48345 | 12/1997 | A61B 17/39 |
| WO | 97/48346 | 12/1997 | A61B 17/39 |
| WO | 98/03117 | 1/1998 | A61B 17/00 |
| WO | 98/07468 | 2/1998 | A61N 1/40 |
| WO | 98/27879 | 7/1998 | A61B 17/36 |
| WO | 98/27880 | 7/1998 | A61B 17/39 |
| WO | 99/08613 | 2/1999 | A61B 17/36 |
| WO | 99/09919 | 3/1999 | A61B 18/12 |
| WO | 99/17690 | 4/1999 | A61F 7/12 |
| WO | 99/30655 | 6/1999 | A61F 7/12 |
| WO | 99/51155 | 10/1999 | A61B 17/36 |
| WO | 99/51158 | 10/1999 | A61B 17/39 |
| WO | 00/62698 | 10/2000 | A61B 18/14 |
| WO | 01/87154 | 5/2001 | A61B 5/05 |
| WO | 02/36028 | 5/2002 | A61B 18/12 |
| WO | 02/085230 | 10/2002 | A61B 18/14 |
| WO | 03/005882 | 1/2003 | A61B 18/14 |
| WO | 03/024305 | 3/2003 | |
| WO | 03/047446 | 6/2003 | A61B 18/12 |
| WO | 03/068095 | 8/2003 | A61B 18/14 |
| WO | 2004/050171 | 6/2004 | |
| WO | 2005/125287 | 12/2005 | A61B 18/00 |
| WO | 2006/002337 | 1/2006 | A61B 18/14 |
| WO | 2006/125007 | 11/2006 | A61B 18/14 |

OTHER PUBLICATIONS

BiLAP Generator Settings, Jun. 1991.
BiLAP IFU 910026-001 Rev A for BiLAP Model 3525, J-Hook, 4 pgs, May 20, 1991.
BiLAP IFU 910033-002 Rev A for BiLAP Model 3527, L-Hook; BiLAP Model 3525, J-Hook; BiLAP Model 3529, High Angle, 2 pgs, Nov. 30, 1993.
Codman & Shurtleff, Inc. "The Malis Bipolar Coagulating and Bipolar Cutting System CMC-II" brochure, early, 2 pgs, 1991.
Codman & Shurtleff, Inc. "The Malis Bipolar Electrosurgical System CMC—III Instruction Manual", 15 pgs, Jul. 1991.
Cook et al., "Therapeutic Medical Devices: Application and Design", Prentice Hall, Inc., 3pgs, 1982.
Dennis et al. "Evolution of Electrofulguration in Control of Bleeding of Experimental Gastric Ulcers," Digestive Diseases and Sciences, vol. 24, No. 11, 845-848, Nov. 1979.
Dobbie, A.K., "The Electrical Aspects of Surgical Diathermy, Bio Medical Engineering" *Bio-Medical Engineering* vol. 4, pp. 206-216, May 1969.
Elsasser, V.E. et al., "An Instrument for Transurethral Resection without Leakage of Current" *Acta Medicotechnica* vol. 24, No. 4, pp. 129-134, 1976.
Geddes, "Medical Device Accidents: With Illustrative Cases" CRC Press, 3 pgs, 1998.
Honig, W., "The Mechanism of Cutting in Electrosurgery" *IEEE* pp. 58-65, 1975.
Kramolowsky et al. "The Urological App of Electorsurgery" *J. of Urology* vol. 146, pp. 669-674, 1991.
Kramolowsky et al. "Use of 5F Bipolar Electrosurgical Probe in Endoscopic Urological Procedures" *J. of Urology* vol. 143, pp. 275-277, 1990.
Lee, B et al. "Thermal Compression and Molding of Artherosclerotic Vascular Tissue with Use" JACC vol. 13(5), pp. 1167-1171, 1989.
Letter from Department of Health to Jerry Malis dated Jan. 24, 1991, 3 pgs.
Letter from Department of Health to Jerry Malis dated Jul. 25, 1985, 1 pg.
Letter from Jerry Malis to FDA dated Jul. 25, 1985, 2 pgs.
Lu, et al., "Electrical Thermal Angioplasty: Catheter Design Features, In Vitro Tissue Ablation Studies and In Vitro Experimental Findings," *Am J. Cardiol* vol. 60, pp. 1117-1122, Nov. 1, 1987.
Malis, L., "Electrosurgery, Technical Note," *J. Neursurg.*, vol. 85, pp. 970-975, Nov. 1996.

(56) References Cited

OTHER PUBLICATIONS

Malis, L., "Excerpted from a seminar by Leonard I. Malis, M.D. at the 1995 American Association of Neurological Surgeons Meeting," 1pg, 1995.
Malis, L., "Instrumentation for Microvascular Neurosurgery" *Cerebrovascular Surgery*, vol. 1, pp. 245-260, 1985.
Malis, L., "New Trends in Microsurgery and Applied Technology," *Advanced Technology in Neurosurgery*, pp. 1-16, 1988.
Malis, L., "The Value of Irrigation During Bipolar Coagulation" See ARTC 21602, 1 pg, Apr. 9, 1993.
Nardella, P.C., *SPIE* 1068: pp. 42-49, Radio Frequency Energy and Impedance Feedback, 1989.
O'Malley, Schaum's Outline of Theory and Problems of Basic Circuit Analysis, McGraw-Hill, $2^{nd}$ Ed., pp. 3-5, 1992.
Olsen MD, Bipolar Laparoscopic Cholecstectomy Lecture (marked confidential), 12 pgs, Oct. 7, 1991.
Pearce, John A. "Electrosurgery", pp. 17, 69-75, 87, John Wiley & Sons, New York, 1986.
Pearce, John A., "Electrosurgery", Handbook of Biomedical Engineering, chapter 3, Academic Press Inc., N.Y., pp. 98-113, 1988.
Piercey et al., "Electrosurgical Treatment of Experimental Bleeding Canine Gastric Ulcers" *Gastroenterology* vol. 74(3), pp. 527-534, 1978.
Protell et al., "Computer-Assisted Electrocoagulation: Bipolar v. Monopolar in the Treatment of Experimental Canine Gastric Ulcer Bleeding," *Gastroenterology* vol. 80, No. 3, pp. 451-455, 1981.
Ramsey et al., "A Comparison of Bipolar and Monopolar Diathermy Probes in Experimental Animals", *Urological Research* vol. 13, pp. 99-102, 1985.
Selikowitz et al., "Electric Current and Voltage Recordings on the Myocardium During Electrosurgical Procedures in Canines," *Surgery, Gynecology & Obstetrics*, vol. 164, pp. 219-224, Mar. 1987.
Shuman, "Bipolar Versus Monopolar Electrosurgery: Clinical Applications," *Dentistry Today*, vol. 20, No. 12, 7 pgs, Dec. 2001.
Slager et al. "Spark Erosion of Arteriosclerotic Plaques" *Z. Kardiol.* 76:Suppl. 6, pp. 67-71, 1987.
Slager et al. "Vaporization of Atherosclerotice Plaques by Spark Erosion" *JACC* 5(6): pp. 1382-1386, Jun. 1985.
Stoffels, E. et al., "Investigation on the Interaction Plasma-Bone Tissue", E-MRS Spring Meeting, 1 pg, Jun. 18-21, 2002.
Stoffels, E. et al., "Biomedical Applications of Plasmas", Tutorial presented prior to the $55^{th}$ Gaseous Electronics Conference in Minneapolis, MN, 41 pgs, Oct. 14, 2002.
Stoffels, E. et al., "Plasma Interactions with Living Cells", Eindhoven University of Technology, 1 pg, 2002.
Stoffels, E. et al., "Superficial Treatment of Mammalian Cells using Plasma Needle", J. Phys. D: Appl. Phys. 26, pp. 2908-2913, Nov. 19, 2003.
Stoffels, E. et al., "Plasma Needle", Eindhoven University of Technology, 1 pg, Nov. 28, 2003.
Stoffels, E. et al., "Plasma Physicists Move into Medicine", Physicsweb, 1 pg, Nov. 2003.
Stoffels, E. et al., "Plasma Treated Tissue Engineered Skin to Study Skin Damage", Biomechanics and Tissue Engineering, Materials Technology, 1 pg, 2003.
Stoffels, E. et al., "Plasma Treatment of Dental Cavities: A Feasibility Study", IEEE Transaction on Plasma Science, vol. 32, No. 4, pp. 1540-1542, Aug. 2004.
Stoffels, E. et al., "The Effects of UV Irradiation and Gas Plasma Treatment on Living Mammalian Cells and Bacteria: A Comparative Approach", IEEE Transaction on Plasma Science, vol. 32, No. 4, pp. 1544-1550, Aug. 2004.
Stoffels, E. et al., "Electrical and Optical Characterization of the Plasma Needle", New Journal of Physics 6, pp. 1-14, Oct. 28, 2004.
Stoffels, E. et al., "Where Plasma Meets Plasma", Eindhoven University of Technology, 23 pgs, 2004.
Stoffels, E. et al., "Gas Plasma effects on Living Cells", Physica Scripta, T107, pp. 79-82, 2004.
Stoffels, E. et al., "Plasma Treatment of Mammalian Vascular Cells: A Quantitative Description", IEEE Transaction on Plasma Science, vol. 33, No. 2, pp. 771-775, Apr. 2005.
Stoffels, E. et al., "Deactivation of *Escherichia coli* by the Plasma Needle", J. Phys. D: Appl. Phys. 38, pp. 1716-1721, May 20, 2005.
Stoffels, E. et al., "Development of a Gas Plasma Catheter for Gas Plasma Surgery", XXVIIth ICPIG, Endoven University of Technology, pp. 18-22, Jul. 2005.
Stoffels, E. et al., "Development of a Smart Positioning Sensor for the Plasma Needle", Plasma Sources Sci. Technol. 15, pp. 582-589, Jun. 27, 2006.
Stoffels, E. et al., Killing of S. Mutans Bacteria Using a Plasma Needle at Atmospheric Pressure, IEEE Transaction on Plasma Science, vol. 34, No. 4, pp. 1317-1324, Aug. 2006.
Stoffels, E. et al., "Plasma-Needle Treatment of Substrates with Respect to Wettability and Growth of *Excherichia coli* and *Streptococcus mutans*", IEEE Transaction on Plasma Science, vol. 34, No. 4, pp. 1325-1330, Aug. 2006.
Stoffels, E. et al., "Reattachment and Apoptosis after Plasma-Needle Treatment of Cultured Cells", IEEE Transaction on Plasma Science, vol. 34, No. 4, pp. 1331-1336, Aug. 2006.
Stoffels, E. et al., "UV Excimer Lamp Irradiation of Fibroblasts: The Influence on Antioxidant Homostasis", IEEE Transaction on Plasma Science, vol. 34, No. 4, pp. 1359-1364, Aug. 2006.
Stoffels, E. et al., "Plasma Needle for In Vivo Medical Treatment: Recent Developments and Perspectives", Plasma Sources Sci. Technol. 15, pp. S169-S180, Oct. 6, 2006.
Swain, C.P., et al., "Which Electrode, A Comparison of four endoscopic methods of electrocoagulation in experimental bleeding ulcers" *Gut* vol. 25, pp. 1424-1431, 1987.
Tucker, R. et al., Abstract P14-11, p. 248, "A Bipolar Electrosurgical Turp Loop", Nov. 1989.
Tucker, R. et al. "A Comparison of Urologic Application of Bipolar Versus Monopolar Five French Electrosurgical Probes" *J. of Urology* vol. 141, pp. 662-665, 1989.
Tucker, R. et al. "In vivo effect of 5 French Bipolar and Monopolar Electrosurgical Probes on the Porcine Bladder" *Urological Research* vol. 18, pp. 291-294, 1990.
Tucker, R. et al., "Demodulated Low Frequency Currents from Electrosurgical Procedures," *Surgery, Gynecology and Obstetrics*, 159:39-43, 1984.
Tucker et al. "The interaction between electrosurgical generators, endoscopic electrodes, and tissue," Gastrointestinal Endoscopy, vol. 38, No. 2, pp. 118-122, 1992.
Valley Forge Scientific Corp., "Summary of Safety and Effective Information from 510K", 2pgs, 1991.
Valley Forge's New Products, Clinica, 475, 5, Nov. 6, 1991.
Valleylab SSE2L Instruction Manual, 11 pgs, Jan. 6, 1983.
Valleylab, Inc. "Valleylab Part No. 945 100 102 A" Surgistat Service Manual, pp. 1-46, Jul. 1988.
Wattiez, Arnaud et al., "Electrosurgery in Operative Endoscopy," Electrosurgical Effects, Blackwell Science, pp. 85-93, 1995.
Wyeth, "Electrosurgical Unit" pp. 1181-1202, 2000.
Rand et al., "Effect of Elecctrocautery on Fresh Human Articular Cartilage", J. Arthro. Surg., vol. 1, pp. 242-246, 1985.
European Search Report for EP00123324.6 4 pgs, Mailed Jan. 16, 2001.
European Search Report for EP00928246 4 pgs, Mailed Mar. 7, 2008.
European Search Report for EP09153983 9 pgs, Mailed Apr. 1, 2009.
European Search Report for EP98964730.0 3 pgs, Mailed Nov. 20, 2000.
European Search Report for EP99922855.4 3 pgs, Aug. 2, 2001.
European Search Report for EP05762588 3 pgs, Apr. 12, 2010.
European Search Report for EP06760025.4 5 pgs, Nov. 10, 2010.
PCT International Preliminary Examination Report for PCT/US00/10674 4pgs, Mailed Mar. 7, 2001.
PCT International Preliminary Examination Report for PCT/US98/26624 4pgs, Mailed Oct. 12, 1999.
PCT International Preliminary Examination Report for PCT/US99/10062 3pgs, Jun. 20, 2000.

(56) References Cited

OTHER PUBLICATIONS

PCT International Preliminary Report on Patentability for PCT/US05/22373 4pgs, Dec. 28, 2006.
PCT International Preliminary Report on Patentability for PCT/US06/19095 6pgs, Nov. 20, 2007.
PCT International Search Report for PCT/US00/10674 1 pg, Mailed Jul. 27, 2000.
PCT International Search Report for PCT/US03/38782 1 pg, Mailed Jun. 30, 2004.
PCT International Search Report for PCT/US05/22373 1 pg, Mailed Oct. 3, 2006.
PCT International Search Report for PCT/US06/19095 2 pgs, Mailed Oct. 4, 2007.
PCT International Search Report for PCT/US96/08077 1 page, Mailed Sep. 16, 1996.
PCT International Search Report for PCT/US98/26624 1 page, Mailed Mar. 3, 1999.
PCT International Search Report for PCT/US99/10062 1 pg, Mailed Aug. 23, 1999.
UK Search Report for GB1111622.5 4pgs, Mailed Oct. 26, 2011.
UK Search Report for GB1202275.2 7pgs May 11, 2012.
UK Search Report for GB1202275.2 5pgs Sep. 12, 2014.
UK Combined Search and Exam Report for GB1404394.7 6pgs Sep. 17, 2014.
CN First OA for CN app No. 201410129644.0 dated Sep. 2, 2015, 28 pages, Sep. 2, 2015.

\* cited by examiner

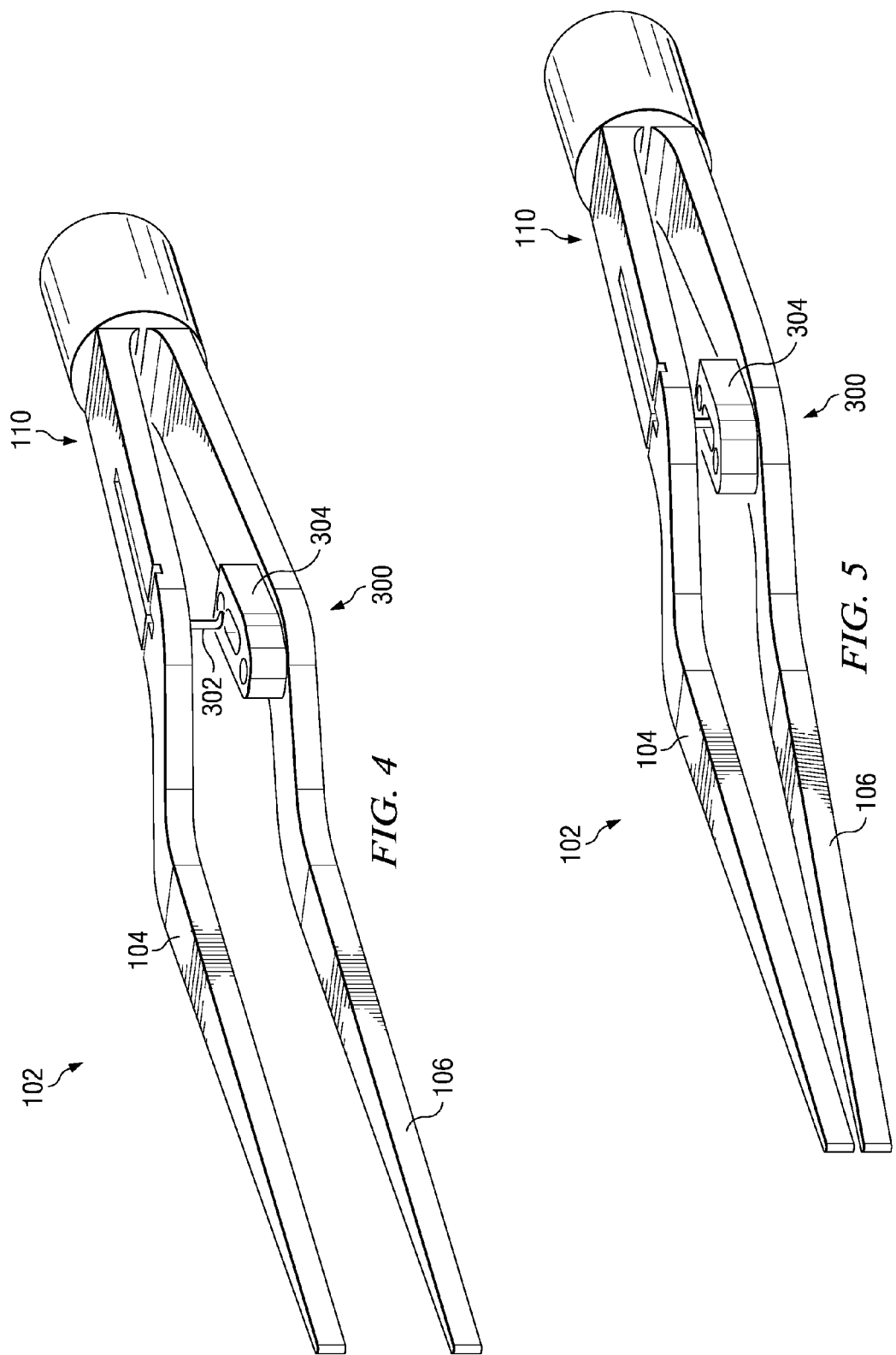

PLASMA BIPOLAR FORCEPS

CROSS REFERENCE TO RELATED APPLICATIONS

The present invention claims priority to U.S. Provisional Application No. 61/532,474, entitled Plasma Bipolar Forceps, filed Sep. 8, 2011, the complete disclosure of which is hereby incorporated by reference in its entirety for all purposes.

FIELD OF THE INVENTION

The present invention relates to electrosurgery and in particular, to electrosurgical bipolar forceps.

BACKGROUND

The field of electrosurgery includes a number of loosely related surgical techniques which have in common the application of electrical energy to modify the structure or integrity of patient tissue. Electrosurgical procedures usually operate through the application of very high frequency currents to cut or ablate tissue structures, where the operation can be monopolar or bipolar. Monopolar techniques rely on a separate electrode for the return of current that is placed away from the surgical site on the body of the patient, and where the surgical device defines only a single electrode pole that provides the surgical effect. Bipolar devices comprise two or more electrodes on the same support for the application of current between their surfaces.

Electrosurgical procedures and techniques are particularly advantageous because they generally reduce patient bleeding and trauma associated with cutting operations. Additionally, electrosurgical ablation procedures, where tissue surfaces and volume may be reshaped, cannot be duplicated through other treatment modalities.

Radiofrequency (RF) energy is used in a wide range of surgical procedures because it provides efficient tissue resection and coagulation and relatively easy access to the target tissues through a portal or cannula. Conventional monopolar high frequency electrosurgical devices typically operate by creating a voltage difference between the active electrode and the target tissue, causing an electrical arc to form across the physical gap between the electrode and tissue. At the point of contact of the electric arcs with tissue, rapid tissue heating occurs due to high current density between the electrode and tissue. This high current density causes cellular fluids to rapidly vaporize into steam, thereby producing a "cutting effect" along the pathway of localized tissue heating. Thus, the tissue is parted along the pathway of evaporated cellular fluid, inducing undesirable collateral tissue damage in regions surrounding the target tissue site. This collateral tissue damage often causes indiscriminate destruction of tissue, resulting in the loss of the proper function of the tissue. In addition, the device does not remove any tissue directly, but rather depends on destroying a zone of tissue and allowing the body to eventually remove the destroyed tissue.

Present electrosurgical devices used for cutting and dissection, such as monopolar electrocautery instruments, are able to cut and coagulate tissue, but cause high levels of collateral thermal damage to surrounding tissue. This limits the use of the monopolar electrocautery devices to relatively "safe" areas away from sensitive structures such as blood vessels and nerves. In comparison, a traditional bipolar forceps may be used routinely for coagulation of small to medium sized vessels and may be preferred over monopolar electrocautery devices in the vicinity of sensitive structures because use of traditional bipolar forceps typically results in much less collateral thermal damage due to the localization of energy around the active and return electrodes at the tip of the device. However, these bipolar forceps do not have the ability to effectively cut or dissect tissue, requiring a physician needing to cut coagulated tissue to select another instrument (scissors, monopolar electrocautery, etc.) to complete the dissection. The necessity of so many instruments for one surgical procedure requires frequent switching between instruments, adding significant time to the procedure and frustration for the physician. Additionally, vessel sealing solutions presently exist for use where coagulation is desired and can typically involve use of sutures, clips, or energy-based devices to heat, seal, and/or cut large blood vessels. However, these devices are limited in that they do not provide fine dissection of tissue.

Accordingly, improved systems and methods in the configuration of surgical forceps are still desired with the ability to perform fine dissection of tissue, while preserving the ability to coagulate vessels and tissue. In particular, improved systems designed to integrate plasma-based cutting combined with effective coagulation abilities into a pair of bipolar forceps would provide a competitive advantage.

BRIEF DESCRIPTION OF THE DRAWINGS

For a detailed description of exemplary embodiments, reference will now be made to the accompanying drawings in which:

FIG. 4 shows a plasma bipolar forceps in an open condition in accordance with at least some embodiments;

FIG. 5 shows a plasma bipolar forceps in a closed position in accordance with at least some embodiments;

NOTATION AND NOMENCLATURE

Figure 1:
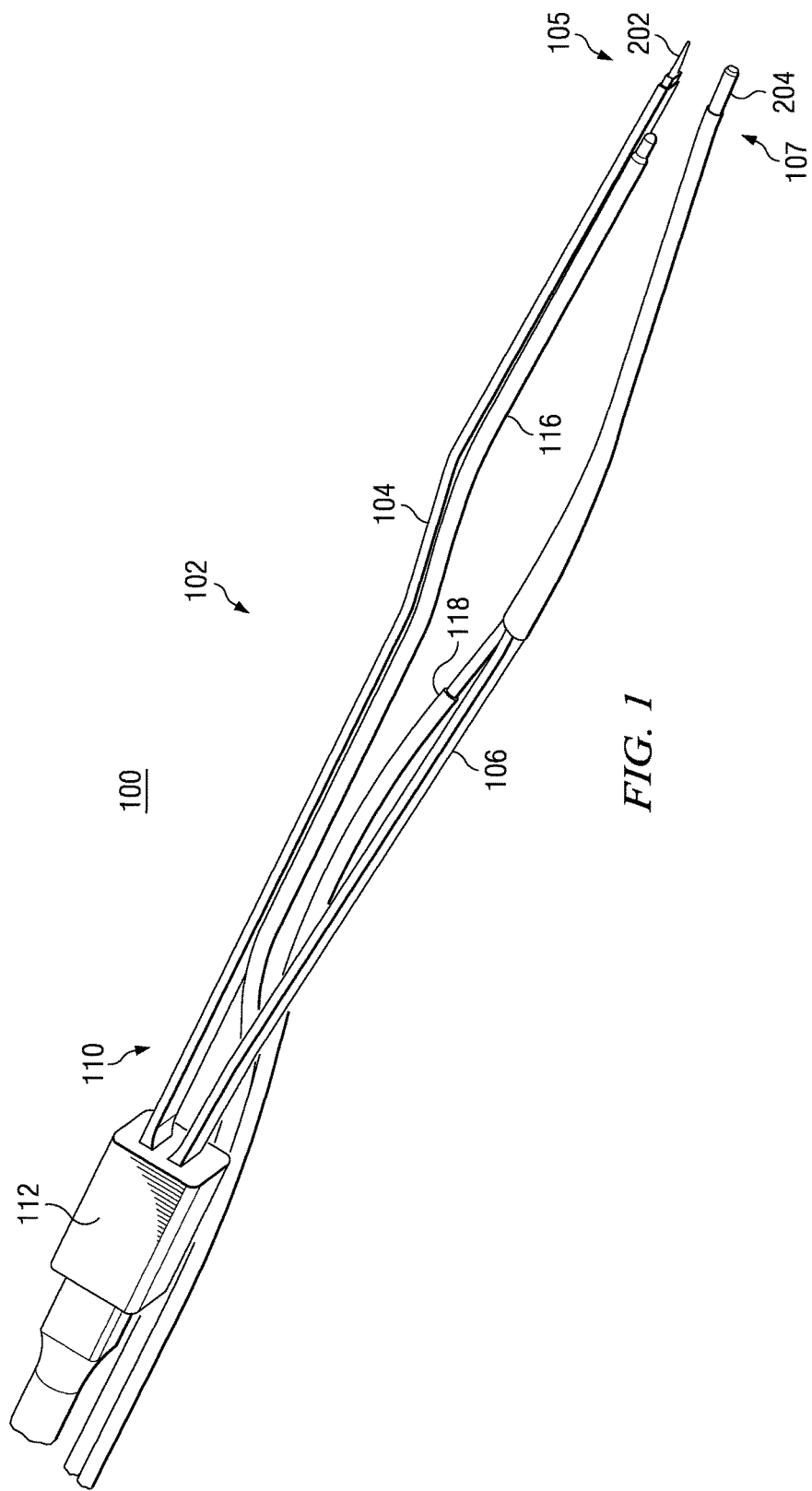
FIG. 1 shows a plasma bipolar forceps device in accordance with at least some embodiments.

Certain terms are used throughout the following description and claims to refer to particular system components. As one skilled in the art will appreciate, companies that design and manufacture electrosurgical systems may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . " Also, the term "couple" or "couples" is intended to mean either an indirect or direct connection.

Thus, if a first device couples to a second device, that connection may be through a direct connection or through an indirect electrical connection via other devices and connections.

Reference to a singular item includes the possibility that there are plural of the same items present. More specifically, as used herein and in the appended claims, the singular forms "a," "an," "said" and "the" include plural references unless the context clearly dictates otherwise. It is further noted that the claims may be drafted to exclude any optional element. As such, this statement serves as antecedent basis for use of such exclusive terminology as "solely," "only" and the like in connection with the recitation of claim elements, or use of a "negative" limitation. Lastly, it is to be appreciated that unless defined otherwise, all technical and scientific terms used herein have the same meaning as commonly understood by one of ordinary skill in the art to which this invention belongs.

"Active electrode" shall mean an electrode of an electrosurgical wand which produces an electrically-induced tissue-altering effect when brought into contact with, or close proximity to, a tissue targeted for treatment.

"Return electrode" shall mean an electrode of an electrosurgical wand which serves to provide a current flow path for electrons with respect to an active electrode, and/or an electrode of an electrical surgical wand which does not itself produce an electrically-induced tissue-altering effect on tissue targeted for treatment.

A fluid conduit said to be "within" an elongate shaft shall include not only a separate fluid conduit that physically resides within an internal volume of the elongate shaft, but also situations where the internal volume of the elongate shaft is itself the fluid conduit.

Where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

DETAILED DESCRIPTION

Before the various embodiments are described in detail, it is to be understood that this invention is not limited to particular variations set forth herein as various changes or modifications may be made, and equivalents may be substituted, without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

FIG. 1 illustrates an electrosurgical system 100 in accordance with at least some embodiments. In particular, the electrosurgical system comprises a plasma bipolar forceps 102 (hereinafter "forceps") operable to be coupled to an electrosurgical controller (not shown). Forceps 102 comprises legs 104 and 106 each defining a distal end portion 105, 107, where at least some electrodes are disposed. Forceps 102 may be referred to as bayonet-style surgical forceps, with 0.5-2.0 mm size tips. The forceps 102 further define a handle or proximal end 110, where a physician grips the forceps 102 during surgical procedures. The forceps 102 further comprises a flexible multi-conductor cable 112 housing a plurality of electrical leads (not specifically shown in FIG. 1), and the flexible multi-conductor cable 112 electrically couples forceps 102 to the electrosurgical generator/controller.

In some embodiments the forceps 102 has one or more fluid conduits operable to be coupled to externally accessible tubular members (for access to a fluid receptacle or wall suction). As illustrated, the forceps 102 has a flexible tubular member 116 and a second flexible tubular member 118. In some embodiments, the flexible tubular member 116 is used to provide electrically conductive fluid (e.g., saline) to the distal end portion 105 of the leg 104. Likewise in some embodiments, flexible tubular member 118 is used to provide aspiration to the distal end portion 107 of the leg 106.

The electrosurgical system 100 of the various embodiments may have a variety of operational modes. One such mode employs Coblation® technology. In particular, the assignee of the present disclosure is the owner of Coblation technology. Coblation technology involves the application of a radio frequency (RF) signal between one or more active electrodes and one or more return electrodes of the wand 102 to develop high electric field intensities in the vicinity of the target tissue. The electric field intensities may be sufficient to vaporize an electrically conductive fluid over at least a portion of the one or more active electrodes in the region between the one or more active electrodes and the target tissue. The electrically conductive fluid may be inherently present in the body, such as blood, or in some cases extracelluar or intracellular fluid. In other embodiments, the electrically conductive fluid may be a liquid or gas, such as isotonic saline. In some embodiments, such as surgical procedures on a disc between vertebrae, the electrically conductive fluid is delivered in the vicinity of the active electrode and/or to the target site by the wand 102, such as by way of the internal passage and flexible tubular member 116.

When the electrically conductive fluid is heated to the point that the atoms of the fluid vaporize faster than the atoms recondense, a gas is formed. When sufficient energy is applied to the gas, the atoms collide with each other causing a release of electrons in the process, and an ionized gas or plasma is formed (the so-called "fourth state of matter"). Stated otherwise, plasmas may be formed by heating a gas and ionizing the gas by driving an electric current through the gas, or by directing electromagnetic waves into the gas. The methods of plasma formation give energy to free electrons in the plasma directly, electron-atom collisions liberate more electrons, and the process cascades until the desired degree of ionization is achieved. A more complete description of plasma can be found in Plasma Physics, by R. J. Goldston and P. H. Rutherford of the Plasma Physics Laboratory of Princeton University (1995), the complete disclosure of which is incorporated herein by reference.

As the density of the plasma becomes sufficiently low (i.e., less than approximately 1020 atoms/cm$^3$ for aqueous solutions), the electron mean free path increases such that subsequently injected electrons cause impact ionization within the plasma. When the ionic particles in the plasma layer have sufficient energy (e.g., 3.5 electron-Volt (eV) to 5 eV), collisions of the ionic particles with molecules that make up the target tissue break molecular bonds of the target tissue, dissociating molecules into free radicals which then combine into gaseous or liquid species. Often, the electrons in the plasma carry the electrical current or absorb the electromagnetic waves and, therefore, are hotter than the ionic particles. Thus, the electrons, which are carried away from the target tissue toward the active or return electrodes, carry most of the plasma's heat, enabling the ionic particles to break apart the target tissue molecules in a substantially non-thermal manner.

By means of the molecular dissociation (as opposed to thermal evaporation or carbonization), the target tissue is volumetrically removed through molecular dissociation of larger organic molecules into smaller molecules and/or atoms, such as hydrogen, oxygen, oxides of carbon, hydrocarbons and nitrogen compounds. The molecular dissociation completely removes the tissue structure, as opposed to dehydrating the tissue material by the removal of liquid within the cells of the tissue and extracellular fluids, as occurs in related art electrosurgical desiccation and vaporization. A more detailed description of the molecular dissociation can be found in commonly assigned U.S. Pat. No. 5,697,882, the complete disclosure of which is incorporated herein by reference.

In addition to the Coblation mode, the electrosurgical system 100 of FIG. 1 may also in particular situations be useful for sealing larger vessels (e.g., on the order of about 1-5 mm in diameter), when used in what is known as a coagulation mode. Thus, the system of FIG. 1 may have an ablation mode where RF energy at a first voltage is applied to one or more active electrodes sufficient to effect molecular dissociation or disintegration of the tissue, and the system of FIG. 1 may have a coagulation mode where RF energy at a second, lower voltage is applied to one or more active electrodes (either the same or different electrode(s) as the ablation mode) sufficient to heat, shrink, seal, fuse, and/or achieve homeostasis of severed vessels within the tissue. In addition, pressure may be applied between the legs of the forceps to compress a target vessel, allowing better penetration of the energy to help seal the vessel.

The energy density produced by electrosurgical system 100 at the distal end of the wand 102 may be varied by adjusting a variety of factors, such as: the number of active electrodes; electrode size and spacing; electrode surface area; asperities and/or sharp edges on the electrode surfaces; electrode materials; applied voltage; current limiting of one or more electrodes (e.g., by placing an inductor in series with an electrode); electrical conductivity of the fluid in contact with the electrodes; density of the conductive fluid; and other factors. Accordingly, these factors can be manipulated to control the energy level of the excited electrons. Because different tissue structures have different molecular bonds, the electrosurgical system 100 may be configured to produce energy sufficient to break the molecular bonds of certain tissue but insufficient to break the molecular bonds of other tissue. For example, fatty tissue (e.g., adipose) has double bonds that require an energy level higher than 4 eV to 5 eV (i.e., on the order of about 8 eV) to break. Accordingly, the Coblation® technology in some operational modes does not ablate such fatty tissue; however, the Coblation technology at the lower energy levels may be used to effectively ablate cells to release the inner fat content in a liquid form. Other modes may have increased energy such that the double bonds can also be broken in a similar fashion as the single bonds (e.g., increasing voltage or changing the electrode configuration to increase the current density at the electrodes).

A more complete description of the various phenomena can be found in commonly assigned U.S. Pat. Nos. 6,355,032; 6,149,120 and 6,296,136, the complete disclosures of which are incorporated herein by reference.

Figure 2:
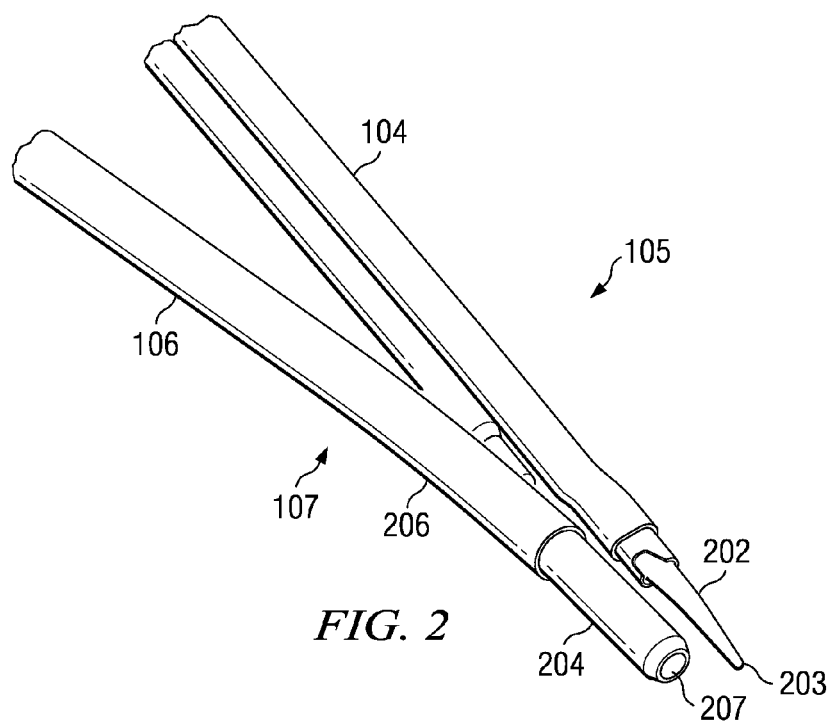
FIG. 2 shows a distal portion of a plasma bipolar forceps in a closed position in accordance with at least some embodiments.
Figure 3:
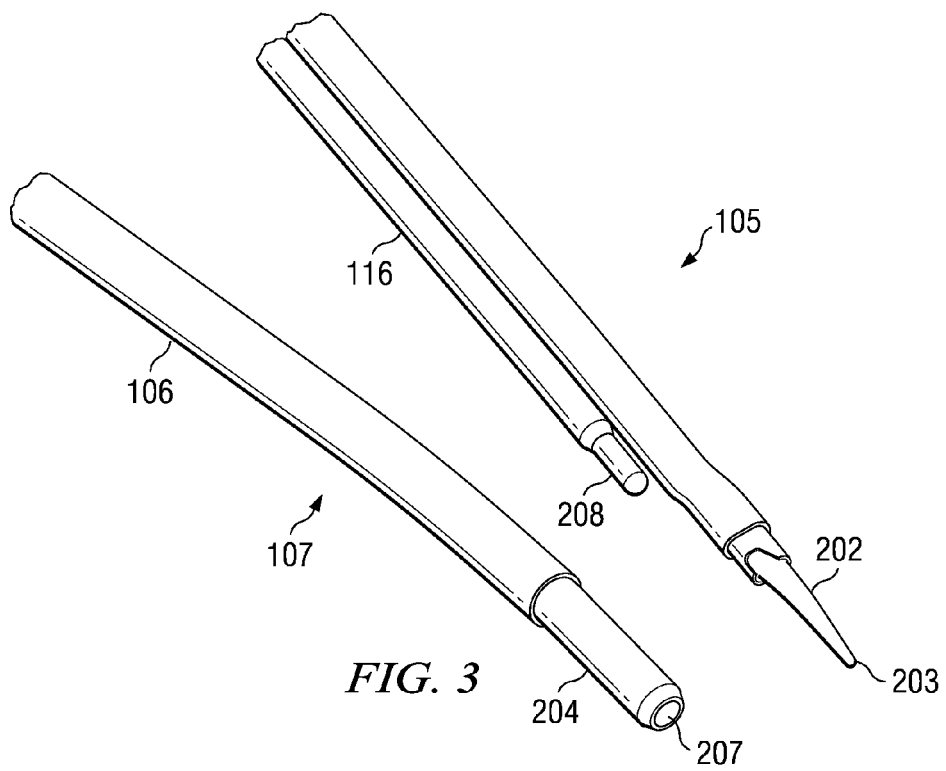
FIG. 3 shows a distal portion of a plasma bipolar forceps in an open position in accordance with at least some embodiments.

Referring now to FIGS. 2 and 3, a discreet portion of the distal end portion 105 of leg 104 is electrically connected to the controller and configured as active electrode 202. Likewise, a discreet portion of distal end portion 107 of leg 106 is electrically connected to the controller and configured as return electrode 204 for completing the current path between active electrode 202 and the controller. The exposed area of active electrode 202 may be partially insulated to enable quick initiation of plasma for cutting (i.e., maintain a smaller exposed surface area on the active electrode as compared to the return electrode). The outer edges of active electrode 202 can have localized areas of high current density, such as sharpened edges, notches, or other features to preferentially initiate plasma on the desired cutting surfaces. Likewise, the inside surfaces of active electrode 202 can be smooth and rounded to help minimize plasma formation on non-cutting surfaces that are primarily intended for resistive heating in coagulation mode.

Return electrode 204 is preferably a semi-annular member defining the exterior of distal end portion 107, and a distal portion of return electrode 204 is preferably exposed. At least a proximal portion of return electrode 204 is disposed within an electrically insulative sheath 206, which is typically formed as one or more electrically insulative sheaths or coatings, such as polytetrafluoroethylene, polyimide, and the like. The provision of the electrically insulative sheath 206 encircling over a portion of return electrode 204 prevents direct electrical contact between return electrode 204 and any adjacent body structure or the surgeon. Such direct electrical contact between a body structure (e.g., vessel) and an exposed common electrode member 204 could result in unwanted heating and necrosis of the structure at the point of contact causing necrosis. Return electrode 204 is preferably formed from an electrically conductive material, usually metal, which is selected from the group consisting of stainless steel alloys, platinum or its alloys, titanium or its alloys, molybdenum or its alloys, and nickel or its alloys.

Forceps 102 are operable in manner consistent with similar grasping-type devices, in that concurrent pressure applied to the outer surface of each the legs 104, 106 actuates the legs 104, 106, and particularly the distal end portions 105, 107, toward one another. As such, the legs 104, 106 of forceps 102 may be selectively positioned in either an open position (i.e., legs 104, 106 are separated by some distance) as shown in FIG. 3, or a closed position (i.e., legs 104, 106 are positioned in relatively close proximity to one another) as shown in FIG. 2. Forceps 102 is designed to provide optimal plasma formation (and hence, optimal cutting performance) when legs 104, 106 are disposed in the closed position, although distal end portions 105, 107 must be spaced a certain distance to enable plasma formation without permitting arcing between active electrode 202 and return electrode 204. The preferred distance between distal end portions 105, 107 is between 0.020-0.050 inches. However, active electrode 202 could still provide a cutting ability when distal end portions 105, 107 are separated as well. In certain embodiments, a small stopper (not shown) may be used to ensure distal end portions 105, 107 never get closer than a preferred and predetermined distance to prevent arcing between active electrode 202 and return electrode 204. Further, a provision of suitable insulative material could be used to maintain the gap between distal end portions 105, 107 when forceps 102 is disposed in its closed position.

In addition, in certain embodiments the inside edge of active electrode 202 may be temporarily insulated when forceps 102 are configured in the closed position, which is the preferential position when forceps 102 are used for cutting. The placement of additional insulation on the inside edge of active electrode 202 helps prevent plasma from forming on that surface, enabling plasma to preferentially form on the outside edge and tip of active electrode 202. In certain embodiments, the insulative material could be mounted on return electrode 204, so that it covers active electrode 202 when the forceps 102 are in the closed position. Alternatively, the placement of the additional insulation may be on distal tip 105 and arranged to create a staggered effect as compared to the exposed surface of return electrode 204 on distal tip 107, where the insulated surface on leg 104 extends farther distally than the insulated surface of leg 106 (see FIG. 2). When the forceps 102 are in the open position and used for clamping or coagulation of a band of tissue or vessels, the full active electrode area is exposed for maximum current delivery and resistive heating through tissue to provide hemostasis.

As discussed above, the forceps 102 is ideally configured for plasma formation and cutting operation when disposed in its closed position. In the closed position, active electrode 202 provides for fine dissection particularly at its most distal tip 203. However, the outside edge of active electrode may also be suitably utilized for plasma-mediated tissue dissection when activated in the closed position. It also follows that plasma formation and the ability to cut tissue adjacent to active electrode 202 is possible when the forceps is configured in the open position. For example, a physician may grasp a band of tissue between legs 104, 106, and then activate the plasma initiation on the surface of active electrode 202 to effective cut and sever the band of engaged tissue.

In some embodiments saline is delivered to the area of forceps 102 placed adjacent to the surgical field, possibly to aid in plasma creation. Specifically, forceps 102 may have integrated suction and saline delivery for added functionality. Saline delivery is required for optimal formation of plasma, but it also can be used to help flush the surgical field if blood is encountered without the use of an external syringe. Referring to FIG. 3, discharge aperture 208 is illustrated in the vicinity of the distal end portion 105 and in proximity to active electrode 202. The discharge aperture 208 is fluidly coupled to the flexible tubular member 116 (FIG. 1) of forceps 102. Thus, saline or other fluid may be pumped into the flexible tubular member 116 (FIG. 1) and discharged through discharge aperture 208 to further aid in developing consistent wetting around the exposed surface of active electrode 202 and return electrode 204 ideal for efficient plasma formation.

More particularly, saline delivery is accomplished via discharge aperture 208, which is integrated on the inside edge of the active electrode 202 and allows the saline to wick down between distal end portions 105, 107 to form a fluid meniscus between the active and return electrodes. When operating the forceps 102 in closed position, it is preferable that saline delivery provide good wetting of the active and return electrodes so that a saline meniscus forms between distal end portions 105, 107. This meniscus is maintained and replenished by the saline delivery and kept in balance with integrated suction at the distal end of the return electrode. The saline also wicks best to distal end portions 105, 107 when there is a slight angle between distal end portions 105, 107, with the narrowest portion being present at the most distal end. This helps takes advantage of capillary action to draw the fluid electrodes for better wetting and plasma formation at active electrode 202.

In yet still further embodiments, aspiration is provided at the area of the forceps 102 placed adjacent to the surgical field. FIGS. 2 and 3 illustrate aspiration aperture 207 (i.e., suction port 207) disposed through return electrode 204. Suction is integrated inside leg 106 of the return electrode 204 (through a hypo tube) and connected to wall suction via flexible tubular member 118. Suction port 207 provides a path to aspirate the area near the surgical field, such as to remove excess fluids, ablative by-products, and remnants of ablation created by active electrode 202. The location of suction port 207 further provides for ample wetting of the active and return electrodes, with the saline flowing out from discharge aperture 208 and then being pulled toward active electrode 202 by the fluid flow induced from suction port 207. Without being bound to theory, providing broader wetting of the exposed surface of return electrode 204, enabling more uniform plasma formation particularly on active electrode 202.

Integrated suction via suction port 207 for evacuating the saline helps maintain a dry field for identification of tissue and fine dissection. Integrated suction also allows rapid evacuation of blood from a bleeding vessel to localize the origin of the bleeding for effective coagulation application. Suction port 207 is preferentially positioned at the distal end of the return electrode 204, so that suction helps draw saline to the tip for good wetting and plasma formation, and also optimally positioned to evacuate fluids from the surgical field (e.g., saline, blood). In certain embodiments, discharge aperture 208 and suction port 207 may be integrated on the same legs of forceps 102, or swapped to the opposing sides as current described.

As shown for example in FIGS. 2 and 3, return electrode 204 is not directly connected to active electrode 202. To complete a current path so that active electrode 202 is electrically connected to return electrode 204 in the presence of a target tissue, electrically conducting liquid (e.g., isotonic saline) is caused to flow along liquid paths emanating from discharge aperture 208 toward suction port 207, and contacting both return electrode 204 and active electrode 202. When a voltage difference is applied between active electrode 202 and return electrode 204, high electric field intensities will be generated at active electrode 202. As current flows from active electrode 202 to the return electrode 204 in the presence of electrically conductive fluid, the high electric field intensities cause ablation of target tissue adjacent active electrode 202.

The ergonomic configuration forceps 102 affords some unique tissue manipulation and visualization abilities versus other surgical instruments. This includes the ability to open/close legs 104, 106 to grasp tissue or influence the extent of thermal penetration. The preferred length of legs 104, 106 also provide good visualization of the targeted tissue by providing a clear view between distal end portions 105, 107 for precise manipulation and positioning. The forceps 102 can be used similar to other bipolar forceps for coagulation of small vessels and tissue by either positioning the distal end portions 105, 107 with a slight gap on the targeted tissue, or by grasping a vessel or band of tissue, or even sliding the distal end portions 105, 107 along a band of tissue or vessel to provide hemostasis. In addition to coagulation, forceps 102 have the unique ability to perform plasma-mediated cutting and fine dissection of tissue and vessels when activated in ablate/cut mode.

Figure 6:
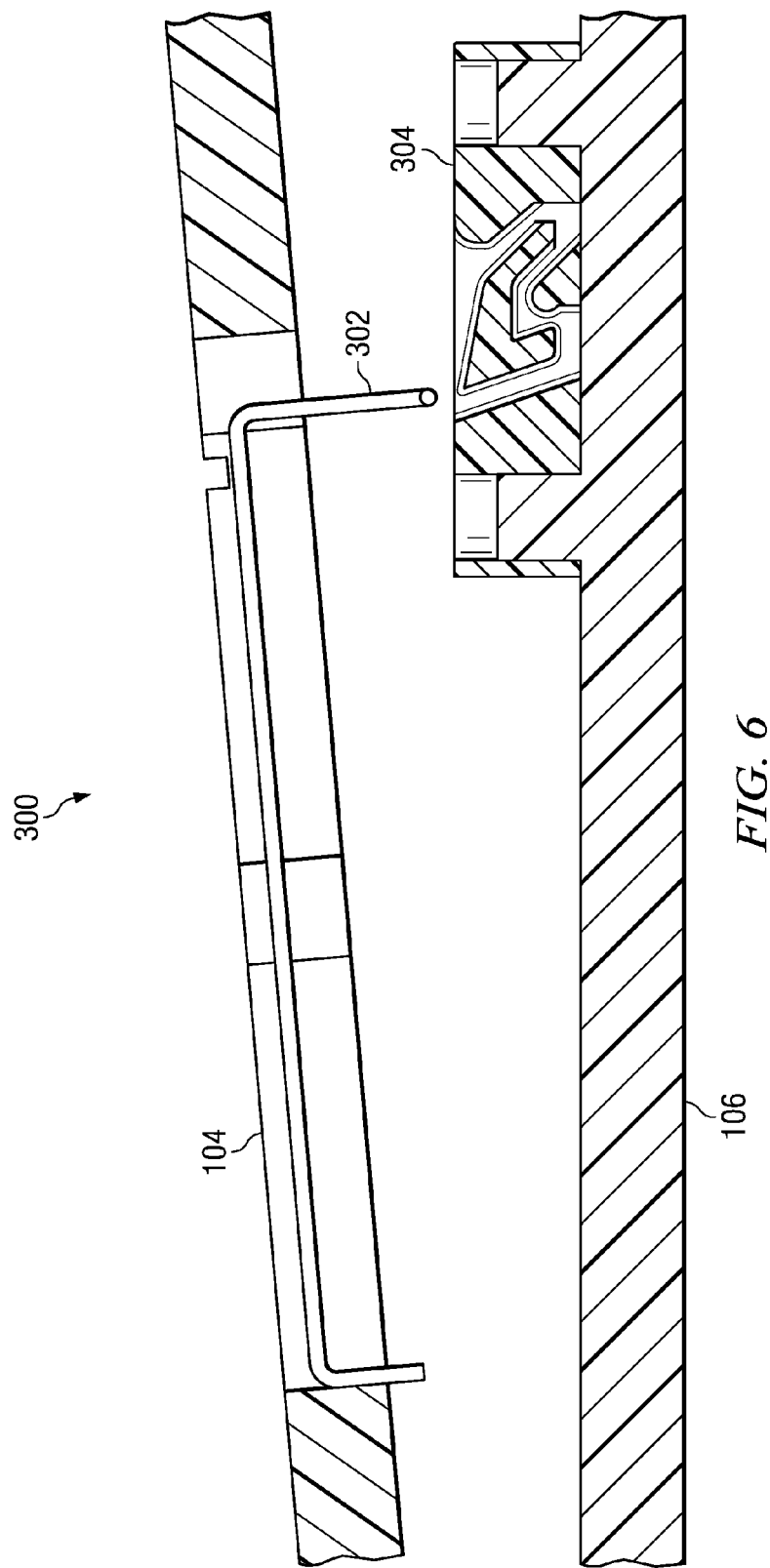
FIG. 6 shows a partial cross-sectional view of a latch mechanism for a plasma bipolar forceps in accordance with at least some embodiments.

Referring now to FIGS. 4-6, in certain embodiments a latch mechanism 300 can also be used to keep the forceps 102 closed, maintaining the optimal gap between distal end portions 105, 107 for plasma formation. Latch mechanism 300 comprises a spring pin 302 disposed on leg 104 and a detent 304 disposed on leg 106 (although it is contemplated that the spring pin and detent may swap positions and be respectively located on opposite legs), and provides a similar function to a ballpoint pen with retractable mechanism. In operation, detent 304 is engaged by spring pin 302 such that legs 104, 106 are retained in the closed position upon initial engagement by a single compression motion that positions the legs in proximity to one another.

Upon engagement of the spring pin 302 within detent 304, a first follower arm of spring pin 302 is forced into the dual-track cam system of detent 304 to secure spring pin 302 within detent 304. A subsequent compression of the legs 104, 106 releases a second follower arm of the spring pin 302 from engagement within the detent 304. The dual-track cam system of detent 304 and its interplay with the two follower arms of spring pin 302 that engage in the tracks at different positions provide a robust latching mechanism for repeated use. The mechanism can also be made primarily of plastic or other materials to provide an insulating layer between the active and return electrode legs.

Figure 7:
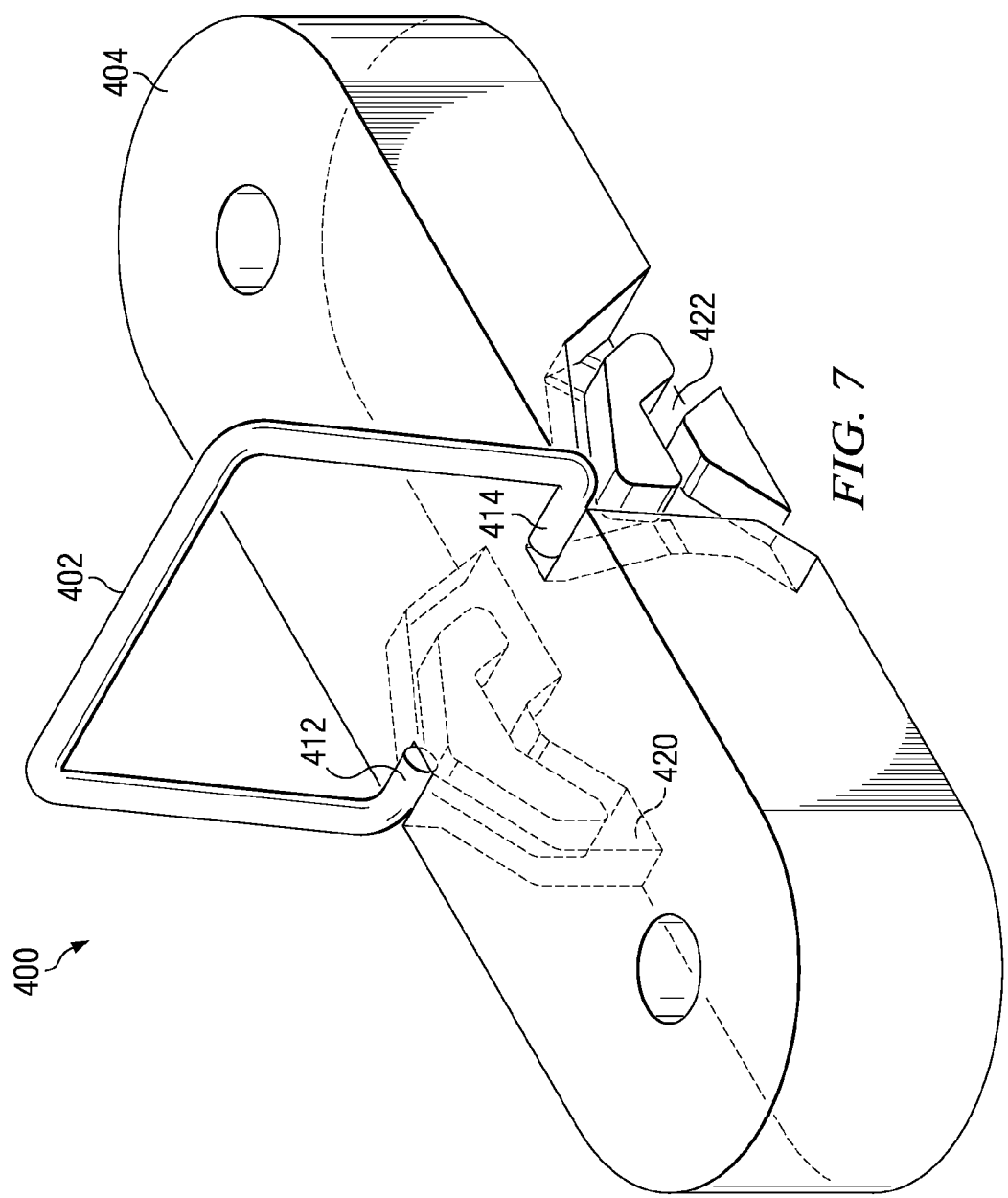
FIG. 7 shows a perspective view of a latch mechanism including a first arm and a second arm engaged in a first track and second track respectively.

FIG. 7 shows a perspective view of a latch mechanism 400 including spring 402 and detent or support 404. Pin 402 is shown including a first arm 412 and a second arm 414. The first arm 412 and second arm 414 are shown engaged in a first track 420 and a second track 422 of a multi- or dual-track system of support 404. As will be described in more detail herein, the arms and tracks of the latch cooperate together to conveniently close and open the forceps upon a first and a second push.

FIGS. 8a-8e show a partial cross section of the latch 400 shown in FIG. 7. In particular, FIGS. 8a-8e illustrate the travel path of each of arms 412, 414 as the forceps' legs are closed and opened.

Figure 8A:
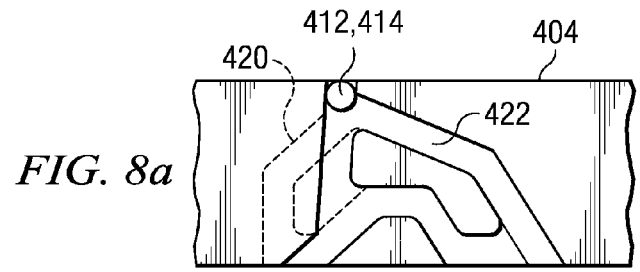
FIGS. 8a-8e show partial cross sections of the latch mechanism shown in FIG. 7 as the bipolar forceps are closed and opened.

FIG. 8a shows the arms 412, 414 in a roughly 12 o'clock starting position. This arm position corresponds to the forceps in an open first position. The arms are axially aligned. The arms and spring are not in tension with one another.

Figure 8B:
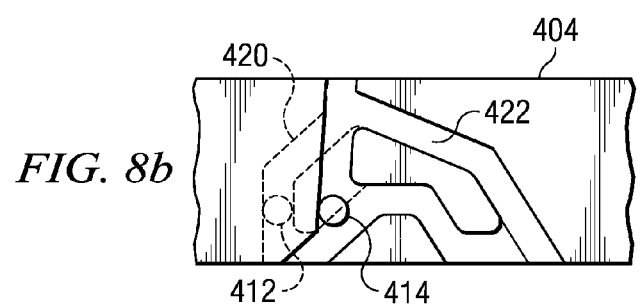

FIG. 8b corresponds to the user providing a first push to the forceps' legs 105, 107. As the user presses on the forceps' legs, pin arms 412 and 414 are moved in a counter clockwise direction to a roughly 9 o'clock position. The arms follow separate guides or tracks. As the user continues to push on the forceps' legs, the arms 412, 414 become non-axially aligned and are placed into tension with one another.

Figure 8C:
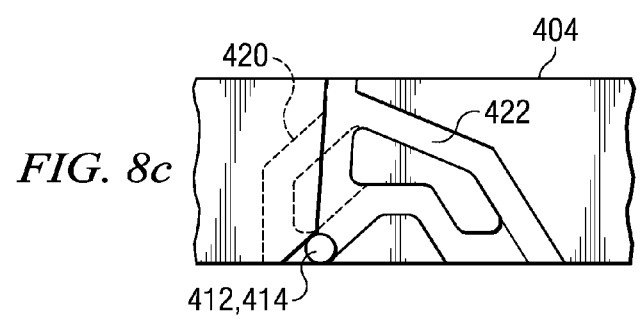

FIG. 8c shows the arms moved further along the tracks in a counter clockwise direction. As the user continues to push on the forceps' legs, the arms approach a track bottom. The arms also are shown axially aligned with one another, thereby relieving some of the tension from the above recited step.

Figure 8D:
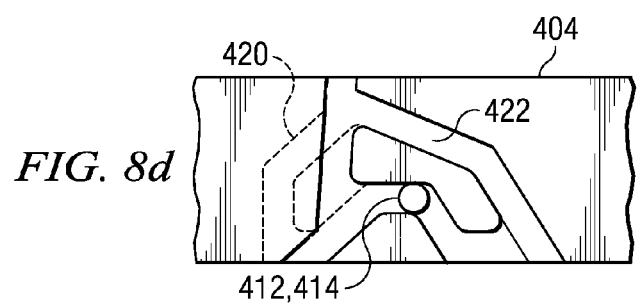

FIG. 8d shows the arms 412, 414 in an intermediate, roughly 6 o'clock position. This substantially tension-free position corresponds to the forceps in a closed second configuration. In particular, when the user releases pressure on the forceps' legs from the first push, the arms 412, 414 snap into the intermediate position shown in FIG. 8d. A ledge on first track 420 prevents the arms from returning to the position shown in FIG. 8c. A ramp on second track 422 urges the arms into the position shown in FIG. 8e, described below.

Figure 8E:
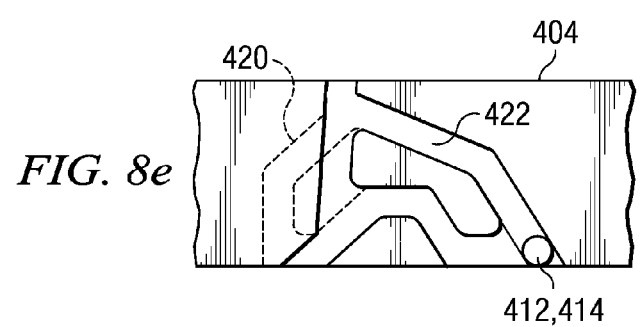

FIG. 8e corresponds to arm position when the user provides a second push to the forceps. In particular, FIG. 8e shows the arms 412, 414 moved in the counter clockwise direction to a roughly 4 o'clock position. A ledge on first track 420 prevents the arms from returning to the position shown in FIG. 8d. Instead, the arms 412, 414 are urged back to the (relatively tension-free neutral) position shown in FIG. 8a, namely, the open or first position.

In this manner, the forceps may be closed and opened by application of a first, and a second push. Each push, in combination with tension from the spring, and the dual track system, locks and unlocks the forceps' legs.

The above discussion is meant to be illustrative of the principles and various embodiments of the present invention. Numerous variations and modifications possible. For example, while in some cases electrodes were designated as upper electrodes and lower electrodes, such a designation was for purposes of discussion, and shall not be read to require any relationship to gravity during surgical procedures. It is intended that the following claims be interpreted to embrace all such variations and modifications.

While preferred embodiments of this disclosure have been shown and described, modifications thereof can be made by one skilled in the art without departing from the scope or teaching herein. The embodiments described herein are exemplary only and are not limiting. Because many varying and different embodiments may be made within the scope of the present inventive concept, including equivalent structures, materials, or methods hereafter though of, and because many modifications may be made in the embodiments herein detailed in accordance with the descriptive requirements of the law, it is to be understood that the details herein are to be interpreted as illustrative and not in a limiting sense.

What is claimed is:

1. An electrosurgical bipolar forceps for use with an electrosurgical controller, said controller comprising a plurality of energy delivery modes including an ablation mode that comprises a plasma and a coagulation mode, said forceps comprising:

a first leg and a second leg, each leg having a proximal and distal end portion and a respective leg length therebetween, wherein the first leg comprises an active electrode;

wherein the second leg comprises a return electrode;

wherein the first leg and second leg lengths are configured to move relative to each other upon application of pressure on an outer surface of each of the first and second leg lengths so as to move the first and second legs between an open first position and a closed second position; and wherein the active electrode and the return electrode are electrically connected to an electrical first lead and a second lead respectively for delivering electrosurgical energy to tissue adjacent to one of the first leg or the second leg; and wherein the forceps further comprise a fluid delivery element having a delivery aperture disposed adjacent the active and return electrode and a fluid aspiration element having an aspiration aperture disposed distal to both the active and return electrode and spaced away from the delivery aperture, the fluid delivery and aspiration elements configured so that fluid flowing from the fluid delivery aperture is drawn by suction induced from the aspiration aperture, distally along an elongate gap defined by the active and return electrodes, so as to improve plasma formation.

2. The forceps of claim 1, wherein the elongate gap defines a first distance when the legs are in the first position, and wherein the elongate gap defines a second distance when the legs are in the second position, and the second distance is substantially less than the first distance.

3. The forceps of claim 2, wherein the second distance ranges from 0.02 to 0.05 inches.

4. The forceps of claim 2, further comprising a latch mechanism for retaining the first and second legs in one of the first and second positions.

5. The forceps of claim 4, wherein the latch mechanism comprises a pin, and a detent, and wherein the pin is disposed on one of the first leg and the second leg, and the detent is disposed on the leg opposite the leg having the pin.

6. The forceps of claim 5, wherein the detent comprises a first track and a second track, the second track having a different shaped path than the first track.

7. The forceps of claim 6, wherein the pin comprises a first follower arm, and the first track is configured to receive and guide the first follower arm when the pin is pushed towards the detent.

8. The forceps of claim 7, wherein the pin comprises a second follower arm, and the second track is configured to receive and guide the second follower arm when the pin is pushed towards the detent.

9. The forceps of claim 8, wherein the pin comprises a spring-like property such that when the first follower arm and second follower arm are axially unaligned, a tension is created in the pin to urge the pin to return to a neutral configuration wherein the first follower arm and second follower arm are axially aligned.

10. The forceps of claim 1, wherein the fluid delivery element comprises a first tubular member that extends along an inner surface of the first leg.

11. The forceps of claim 1, wherein the fluid aspiration element is a second tubular member that defines a portion of the second leg length and the return electrode.

12. The forceps of claim 1, wherein the fluid delivery element and the fluid aspiration element are configured to flow a fluid through their respective apertures at a defined rate, and wherein the aspiration and delivery apertures and the defined flow rate are configured so as to promote and maintain a meniscus along the elongate gap between the active electrode and return electrode.

13. The forceps of claim 12, wherein the active electrode and the return electrode form an angle when the forceps is in the second position, and wherein the angle ranges from 0 to 30 degrees.

14. The forceps of claim 1, wherein the active electrode has a different shape than the return electrode.

15. The forceps of claim 1, wherein the active electrode tapers to a sharp point.

16. The forceps of claim 1, wherein when the first leg and second leg are in the closed second position, the active electrode and the return electrode are spaced apart a distance configured to improve plasma formation without permitting arcing.

17. The forceps of claim 1 wherein the active electrode is shaped to electrosurgically dissect or ablate the tissue adjacent the first leg or the second leg when the controller is in the ablation mode and the forceps are in the closed second position; and wherein the active and return electrodes are shaped to provide hemostasis or coagulation to tissue adjacent the first leg or the second leg when the controller is in the coagulation mode and the forceps are in the first open position or an intermediate position between the closed second position and the first open position.

18. An electrosurgical bipolar forceps for use with an electrosurgical controller, comprising:

a first leg and a second leg, each leg having a proximal and distal end portion and a respective leg length therebetween, wherein the first leg distal end portion comprises an active electrode;

wherein the second leg distal end portion comprises a return electrode;

wherein the first leg and second leg lengths are configured to move relative to each other upon application of pressure on an outer surface of each of the first and second leg lengths so as to move the first and second legs between an open first position and a closed second position; and wherein the active electrode and the return electrode are electrically connected to an electrical first lead and a second lead respectively for delivering electrosurgical energy to tissue adjacent to one of the first leg or the second leg; and wherein the forceps comprise a fluid aspiration element associated with at least one of the legs having an aspiration aperture disposed distal to both the active and return electrode, configured such that fluid is drawn distally along an elongate gap having a length defined by both the active and return electrodes before being aspirated through the aspiration aperture; wherein the fluid is drawn distally at a rate configured to improve the wetting of the active and return electrode with an electrically conductive fluid delivered adjacent the distal end portions, configured to enable more uniform ionized gas formation along the elongate gap when the forceps are in the closed position.

19. An electrosurgical bipolar forceps for use with an electrosurgical controller, comprising:

a first leg and a second leg, each leg having a proximal and distal end portion and a respective leg length therebetween, wherein the first leg distal end portion comprises an active electrode;

wherein the second leg distal end portion comprises a return electrode;

wherein the first leg and second leg lengths are configured to move relative to each other between an open first position and a closed second position; and wherein the active electrode and the return electrode are electrically connected to an electrical first lead and a second lead respectively for delivering electrosurgical energy to tissue adjacent to one of the first leg or the second leg; and wherein the forceps comprise a fluid delivery element associated with at least one of the legs having an aperture disposed adjacent a proximal end of the active and return electrode and a fluid aspiration element associated with at least one of the legs having an aspiration aperture disposed distal to both the active and return electrode, configured such that fluid flows from the fluid delivery aperture and is drawn distally along an elongate gap between the active and return electrodes towards the aspiration aperture.

* * * * *